(12) United States Patent
Rosén et al.

(10) Patent No.: US 11,160,651 B2
(45) Date of Patent: Nov. 2, 2021

(54) INTRAOCULAR LENSES THAT IMPROVE PERIPHERAL VISION

(71) Applicant: AMO GRONINGEN B.V., Groningen (NL)

(72) Inventors: Robert Rosén, Groningen (NL); Franck Emmanuel Gounou, Groningen (NL); Hendrik A. Weeber, Groningen (NL); Carmen Canovas Vidal, Groningen (NL); Marrie H. Van Der Mooren, Engelbert (NL); Mihai State, Groningen (NL); Patricia Ann Piers, Groningen (NL); Aixa Alarcon Heredia, Groningen (NL); Dora Sellitri, Matera (IT)

(73) Assignee: AMO Groningen B.V., Groningen (NL)

( * ) Notice: Subject to any disclaimer, the term of this patent is extended or adjusted under 35 U.S.C. 154(b) by 27 days.

(21) Appl. No.: 16/818,942

(22) Filed: Mar. 13, 2020

(65) Prior Publication Data

US 2020/0214829 A1 Jul. 9, 2020

Related U.S. Application Data

(62) Division of application No. 15/456,356, filed on Mar. 10, 2017, now Pat. No. 10,588,738.
(Continued)

(51) Int. Cl.
*A61F 2/16* (2006.01)

(52) U.S. Cl.
CPC ............ *A61F 2/164* (2015.04); *A61F 2/1613* (2013.01); *A61F 2/1618* (2013.01);
(Continued)

(58) Field of Classification Search
CPC ...................................................... A61F 2/164
See application file for complete search history.

(56) References Cited

U.S. PATENT DOCUMENTS 3,367,734 A  2/1968  Karl et al.
4,581,031 A  4/1986  Koziol et al.
(Continued)

FOREIGN PATENT DOCUMENTS

EP    0343067 A1    11/1989
EP    0457553 A2    11/1991
(Continued)

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.
(Continued)

*Primary Examiner* — Javier G Blanco
(74) *Attorney, Agent, or Firm* — Johnson & Johnson Surgical Vision, Inc.

(57) ABSTRACT

Lenses and methods are provided for improving peripheral and/or central vision for patients who suffer from certain retinal conditions that reduce central vision or patients who have undergone cataract surgery. The lens is configured to improve vision by having an optic configured to focus light incident along a direction parallel to an optical axis at the fovea in order to produce a functional foveal image. The optic is configured to focus light incident on the patient's eye at an oblique angle with respect to the optical axis at a peripheral retinal location disposed at a distance from the fovea, the peripheral retinal location having an eccentricity between −30 degrees and 30 degrees. The image quality at the peripheral retinal location is improved by reducing at least one optical aberration at the peripheral retinal location. The method for improving vision utilizes ocular measure-
(Continued)

ments to iteratively adjust the shape factor of the lens to reduce peripheral refractive errors.

4 Claims, 17 Drawing Sheets

Related U.S. Application Data

(60) Provisional application No. 62/307,241, filed on Mar. 11, 2016, provisional application No. 62/385,702, filed on Sep. 9, 2016.

(52) U.S. Cl.
CPC .......... *A61F 2/1629* (2013.01); *A61F 2/1635* (2013.01); *A61F 2/1637* (2013.01); *A61F 2240/002* (2013.01)

(56) References Cited

U.S. PATENT DOCUMENTS

| | | | |
|---|---|---|---|
| 4,592,630 A | 6/1986 | Okazaki | |
| 4,624,538 A | 11/1986 | MacFarlane | |
| 4,637,697 A | 1/1987 | Freeman | |
| 4,642,112 A | 2/1987 | Freeman | |
| 4,648,878 A | 3/1987 | Kelman | |
| 4,655,565 A | 4/1987 | Freeman | |
| 4,666,446 A | 5/1987 | Koziol et al. | |
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,932,970 A | 6/1990 | Portney | |
| 4,995,714 A | 2/1991 | Cohen | |
| 4,995,715 A | 2/1991 | Cohen | |
| 5,016,977 A | 5/1991 | Baude et al. | |
| 5,056,908 A | 10/1991 | Cohen | |
| 5,066,301 A | 11/1991 | Wiley | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,144,483 A | 9/1992 | Cohen | |
| 5,225,858 A | 7/1993 | Portney | |
| 5,229,797 A | 7/1993 | Futhey et al. | |
| 5,354,334 A | 10/1994 | Fedorov et al. | |
| 5,549,669 A | 8/1996 | Jansen | |
| 5,652,638 A | 7/1997 | Roffman et al. | |
| 5,683,457 A | 11/1997 | Gupta et al. | |
| 5,699,142 A | 12/1997 | Lee et al. | |
| 5,715,091 A | 2/1998 | Meyers | |
| 5,728,156 A | 3/1998 | Gupta et al. | |
| 5,748,282 A | 5/1998 | Freeman | |
| 5,760,871 A | 6/1998 | Kosoburd et al. | |
| 5,777,719 A | 7/1998 | Williams et al. | |
| 5,796,462 A | 8/1998 | Roffman et al. | |
| 5,968,094 A | 10/1999 | Werblin et al. | |
| 5,969,790 A | 10/1999 | Onufryk | |
| 6,126,283 A | 10/2000 | Wen et al. | |
| 6,126,286 A | 10/2000 | Portney | |
| 6,139,145 A | 10/2000 | Israel | |
| 6,142,625 A | 11/2000 | Sawano et al. | |
| 6,183,084 B1 | 2/2001 | Chipman et al. | |
| 6,197,057 B1 | 3/2001 | Peyman et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,464,725 B2 | 10/2002 | Skottun et al. | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,533,814 B1 | 3/2003 | Jansen | |
| 6,536,899 B1 | 3/2003 | Fiala | |
| 6,537,317 B1 | 3/2003 | Steinert et al. | |
| 6,547,822 B1 | 4/2003 | Lang | |
| 6,551,354 B1 | 4/2003 | Ghazizadeh et al. | |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,849,091 B1 | 2/2005 | Cumming | |
| 6,851,803 B2 | 2/2005 | Wooley et al. | |
| 6,913,620 B2 | 7/2005 | Lipshitz | |
| 6,923,539 B2 | 8/2005 | Simpson et al. | |
| 6,923,540 B2 | 8/2005 | Ye et al. | |
| 6,972,033 B2 | 12/2005 | McNicholas | |
| 6,986,578 B2 | 1/2006 | Jones | |
| 7,025,456 B2 | 4/2006 | Morris et al. | |
| 7,025,460 B2 | 4/2006 | Smitth et al. | |
| 7,036,931 B2 | 5/2006 | Lindacher et al. | |
| 7,037,338 B2 | 5/2006 | Nagamoto | |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,186,266 B2 | 3/2007 | Peyman | |
| 7,188,949 B2 | 3/2007 | Bandhauer et al. | |
| 7,238,201 B2 | 7/2007 | Portney et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,410,500 B2 | 8/2008 | Claoue | |
| 7,441,894 B2 | 10/2008 | Zhang et al. | |
| 7,475,986 B2 | 1/2009 | Dai et al. | |
| 7,488,069 B2 | 2/2009 | Hull | |
| 7,503,655 B2 | 3/2009 | Smith, III et al. | |
| 7,615,073 B2 | 11/2009 | Deacon et al. | |
| 7,665,842 B2 | 2/2010 | Ho et al. | |
| 7,766,482 B2 | 8/2010 | Smith, III et al. | |
| 7,871,162 B2 | 1/2011 | Weeber | |
| 7,997,727 B2 | 8/2011 | Ho et al. | |
| 8,057,034 B2 | 11/2011 | Ho et al. | |
| 8,062,361 B2 | 11/2011 | Nguyen et al. | |
| 8,201,943 B2 | 6/2012 | Hammer et al. | |
| 8,206,442 B2 | 6/2012 | Sel et al. | |
| 8,262,728 B2 | 9/2012 | Zhang et al. | |
| 8,382,832 B2 | 2/2013 | Deacon et al. | |
| 8,430,508 B2 | 4/2013 | Weeber | |
| 8,540,365 B2 | 9/2013 | Varnas | |
| 8,862,447 B2 | 10/2014 | Weeber | |
| 9,345,570 B2 | 5/2016 | Sieber et al. | |
| 2002/0044255 A1 | 4/2002 | Ye | |
| 2002/0101564 A1 | 8/2002 | Herrick | |
| 2002/0118337 A1 | 8/2002 | Perrott et al. | |
| 2002/0176049 A1 | 11/2002 | Sakai et al. | |
| 2003/0076478 A1 | 4/2003 | Cox | |
| 2003/0171808 A1 | 9/2003 | Phillips | |
| 2004/0085515 A1 | 5/2004 | Roffman et al. | |
| 2004/0106992 A1 | 6/2004 | Lang et al. | |
| 2004/0111153 A1 | 6/2004 | Woods et al. | |
| 2004/0156014 A1 | 8/2004 | Piers et al. | |
| 2005/0043794 A1 | 2/2005 | Geraghty et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2005/0209692 A1 | 9/2005 | Zhang | |
| 2006/0009816 A1 | 1/2006 | Fang et al. | |
| 2006/0030938 A1 | 2/2006 | Altmann | |
| 2006/0058874 A1 | 3/2006 | Peli | |
| 2006/0066808 A1 | 3/2006 | Blum et al. | |
| 2006/0098162 A1 | 5/2006 | Bandhauer et al. | |
| 2006/0109421 A1 | 5/2006 | Ye et al. | |

(56) References Cited

U.S. PATENT DOCUMENTS

| | | |
|---|---|---|
| 2006/0116763 A1 | 6/2006 | Simpson |
| 2006/0116764 A1 | 6/2006 | Simpson |
| 2006/0116765 A1 | 6/2006 | Blake et al. |
| 2006/0158611 A1 | 7/2006 | Piers et al. |
| 2006/0227286 A1 | 10/2006 | Hong et al. |
| 2006/0238702 A1 | 10/2006 | Glick et al. |
| 2006/0244904 A1 | 11/2006 | Hong et al. |
| 2006/0247766 A1 | 11/2006 | Marin |
| 2007/0052920 A1 | 3/2007 | Stewart et al. |
| 2007/0093891 A1 | 4/2007 | Tabernero et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0212024 A1 | 9/2008 | Lai |
| 2008/0269883 A1 | 10/2008 | Das et al. |
| 2008/0269884 A1 | 10/2008 | Vannoy |
| 2008/0269885 A1 | 10/2008 | Simpson et al. |
| 2008/0269886 A1 | 10/2008 | Simpson et al. |
| 2008/0269890 A1 | 10/2008 | Simpson et al. |
| 2008/0312738 A1 | 12/2008 | Wanders |
| 2009/0018652 A1 | 1/2009 | Hermans et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0198326 A1 | 8/2009 | Zhou et al. |
| 2009/0204211 A1 | 8/2009 | Angelopoulos et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0292354 A1 | 11/2009 | Gontijo et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0100177 A1 | 4/2010 | Zhao |
| 2010/0100178 A1 | 4/2010 | Weeber et al. |
| 2010/0157240 A1 | 6/2010 | Schmid et al. |
| 2010/0161048 A1 | 6/2010 | Schaper, Jr. |
| 2010/0188636 A1 | 7/2010 | Pinto et al. |
| 2010/0204788 A1 | 8/2010 | Van |
| 2011/0130833 A1 | 6/2011 | Scott et al. |
| 2011/0153014 A1 | 6/2011 | Zhang et al. |
| 2011/0279912 A1 | 11/2011 | Fiala |
| 2012/0277857 A1 | 11/2012 | Purchase et al. |
| 2013/0013060 A1 | 1/2013 | Zadno-Azizi |
| 2013/0211515 A1 | 8/2013 | Blum et al. |
| 2013/0226294 A1 | 8/2013 | Van et al. |
| 2014/0022649 A1 | 1/2014 | Eckhardt |
| 2014/0168602 A1 | 6/2014 | Weeber et al. |
| 2014/0253877 A1 | 9/2014 | Li et al. |
| 2015/0005877 A1 | 1/2015 | Wanders |
| 2015/0250583 A1 | 9/2015 | Rosen et al. |
| 2015/0250585 A1 | 9/2015 | Rosen et al. |
| 2015/0265399 A1 | 9/2015 | Rosen et al. |
| 2015/0297342 A1 | 10/2015 | Rosen et al. |
| 2015/0320547 A1 | 11/2015 | Rosen et al. |
| 2016/0067037 A1 | 3/2016 | Rosen et al. |
| 2016/0161364 A1 | 6/2016 | Alarcon |
| 2016/0193040 A1 | 7/2016 | Qureshi et al. |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03000154 A2 | 1/2003 |
| WO | 03009053 A1 | 1/2003 |
| WO | 03022137 A2 | 3/2003 |
| WO | 2004034129 A1 | 4/2004 |
| WO | 2004049979 A1 | 6/2004 |
| WO | 2004068214 A1 | 8/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008065362 A1 | 6/2008 |
| WO | 2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

Atchison D.A., et al., "Shape of the Retinal Surface in Emmetropia and Myopia," Investigative Ophthalmology & Visual Science, Aug. 2005, vol. 46 (8), pp. 2698-2707.

Baskaran K., et al., "Benefit of Adaptive Optics Aberration Correction at Preferred Retinal Locus," Optometry and Vision Science, Sep. 2012, vol. 89 (9), pp. 1417-1423.

Buralli D.A., et al, "Optical Performance of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Cohen A.L., "Practical Design of a Bifocal Hologram Contact Lens or Intraocular Lens," Applied Optics, Jul. 1, 1992, vol. 31 (19), pp. 3750-3754.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Escudero-Sanz I., et al., "Off-Axis Aberrations of a Wide-Angle Schematic Eye Model," Journal of the Optical Society of America. A, Optics, Image Science, and Vision, Aug. 1999, vol. 16 (8), pp. 1881-1891.

Hoffmann, P.C., et al., "Analysis of Biometry and Prevalence Data for Corneal Astigmatism in 23 239 Eyes," Journal of Cataract and Refractive Surgery, Sep. 2010, vol. 36(9), pp. 1479-1485.

Jaeken B., et al., "Comparison of the Optical Image Quality in the Periphery of Phakic and Pseudophakic Eyes," Investigative Ophthalmology & Visual Science, May 1, 2013, vol. 54 (5), pp. 3594-3599.

Jafari-Nodoushan M., et al., "Control-Flow Checking Using Branch Instructions," IEEE/IFIP International Conference on Embedded and Ubiquitous Computing, Dec. 17-20, 2008, pp. 66-72.

Lewis P., et al., "Resolution of Static and Dynamic Stimuli in the Peripheral Visual Field," Vision Research, Aug. 15, 2011, vol. 51 (16), pp. 1829-1834.

Liou H.L., et al., "Anatomically Accurate, Finite Model Eye for Optical Modeling," Journal of Optical Society of America, Aug. 1997, vol. 14 (8), pp. 1684-1695.

(56) References Cited

OTHER PUBLICATIONS

Liou H.L., et al., "The Prediction of Spherical Aberration with Schematic Eyes," Ophthalmic and Physiological Optics, Jan. 1996, vol. 16 (4), pp. 348-354.

Lundstroma L., et al., "Symmetries in Peripheral Ocular Aberrations," Journal of Modern Optics, Mar. 16, 2011, vol. 58 (19-20), pp. 1690-1695.

Marsack J.D., et al., "Metrics of Optical Quality Derived from Wave Aberrations Predict Visual Performance," Journal of Vision, Apr. 2004, vol. 4 (4), pp. 322-328.

Monsoriu J.A., et al., "Devil's Lenses," Optics Express, Oct. 17, 2007, vol. 15 (21), pp. 13858-13864.

Norrby S., et al., "Model Eyes for Evaluation of Intraocular Lenses," Applied Optics, Sep. 7, 2007, vol. 46 (26), pp. 6595-6605.

Oh N., et al., "Control-Flow Checking by Software Signatures," IEEE Transactions on Reliability, Mar. 2, 2002, vol. 51 (2), pp. 111-122.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Rosen R., et al., "Adaptive Optics for Peripheral Vision," Journal of Modern Optics, Jul. 10, 2012, vol. 59 (12), pp. 1064-1070.

Rosen R., et al., "Evaluating the Peripheral Optical Effect of Multifocal Contact Lenses," Ophthalmic and Physiological Optics, Nov. 2012, vol. 32 (6), pp. 527-534.

Rosen R., et al., "Have We Misinterpreted the Study of Hoogerheide Et Al. (1971)?," Optometry and Vision Science, Aug. 2012, vol. 89 (8), pp. 1235-1237.

Rosen R., et al., "Sign-dependent Sensitivity to Peripheral Defocus for Myopes Due to Aberrations," Investigative Ophthalmology & Visual Science, Oct. 17, 2012, vol. 53 (11), pp. 7176-7182.

Rosen R., et al., "Influence of Optical Defocus on Peripheral Vision," Visual Psychophysics and Physiological Optics, Jan. 2011, vol. 52 (1), pp. 318-323.

Rosen R., "Peripheral Vision: Adaptive Optics and Psychophysics," Doctoral Thesis Department of Applied Physics Royal Institute of Technology Stockholm, Sweden Apr. 2013, 86 pages.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Villegas E.A., et al., "Correlation between Optical and Psychophy, Sical Parameters as a Function of Defocus," Optometry and Vision Science, Jan. 1, 2002, vol. 79 (1), pp. 60-67.

INTRAOCULAR LENSES THAT IMPROVE PERIPHERAL VISION

CROSS-REFERENCE TO RELATED APPLICATIONS

This application is a divisional of and claims priority to U.S. patent application Ser. No. 15/456,356, filed Mar. 10, 2017, which claims benefit under 35 U.S.C. § 119(e) of U.S. Provisional Application No. 62/307,241, filed on Mar. 11, 2016, titled "ACHROMAT INTRAOCULAR LENSES THAT IMPROVE PERIPHERAL VISIONS." This application also claims benefit under 35 U.S.C. § 119(e) of U.S. Provisional Application No. 62/385,702, filed on Sep. 9, 2016, titled "INTRAOCULAR LENSES WITH IMPROVED CENTRAL AND PERIPHERAL VISION." The entire content of each of the above identified applications is incorporated by reference herein in its entirety for all it discloses and is made part of this specification.

BACKGROUND

Field

This disclosure generally relates to devices, systems and methods that improve peripheral vision.

Description of Related Art

Intraocular Lenses (IOLs) may be used for restoring visual performance after a cataract or other ophthalmic procedure in which the natural crystalline lens is replaced with or supplemented by implantation of an IOL. When such a procedure changes the optics of the eye, generally a goal is to improve vision in the central field. Recent studies have found that, when a monofocal IOL is implanted, peripheral aberrations are changed, and that these aberrations differ significantly from those of normal, phakic eyes. The predominant change is seen with respect to peripheral astigmatism, which is the main peripheral aberration in the natural eye, followed by sphere, and then higher order aberrations. Such changes may have an impact on overall functional vision, including the ability to drive, the risk of falling, postural stability and/or detection ability.

There are also certain retinal conditions that reduce central vision, such as AMD or a central scotoma. Other diseases may impact central vision, even at a very young age, such as Stargardt disease, Best disease, and inverse retinitis pigmentosa. The visual outcome for patients suffering from these conditions can be improved by improving peripheral vision. Peripheral vision can also be degraded by Glaucoma. Glaucoma affects 2% of the population above the age of 40. Patients with glaucoma gradually lose peripheral vision as a result of damage to the optic nerve. Central vision may get degraded at very late stages of the disease. Significant disabilities in daily life can occur due to glaucoma, including problems with walking, balance, risk of falling and driving. Patients suffering from Glaucoma can benefit from IOLs that improve both central as well as peripheral vision.

SUMMARY

The systems, methods and devices of the disclosure each have several innovative aspects, no single one of which is solely responsible for the desirable attributes disclosed herein.

Patients with central visual field loss caused by e.g. age-related macular degeneration (AMD) rely on their remaining peripheral vision to view objects in the external world. Usually, they develop a preferred retinal locus (PRL), an area on the peripheral retina where the optical image quality is higher than optical image quality at other areas of the retina. They view the PRL either by rotating the eye or the head, thus using eccentric fixation. However, vision at the PRL is much poorer, due to both retinal factors, such as, for example, decreased density of ganglion cells and optical factors, such as, for example, light with the oblique incidence necessary to get to the PRL is degraded by oblique astigmatism and coma. Patients with AMD can receive substantial improvements in vision from refractive correction on their PRL, more so than healthy subjects at similar retinal eccentricity. Patients with Glaucoma who suffer from degraded peripheral visual quality can also benefit from IOLs that improve peripheral optical image quality. Current IOL technologies that are configured to correct refractive errors at the fovea can degrade peripheral optical image quality substantially as compared to the natural lenses. Accordingly, IOLs that can improve image quality at the fovea as well as the peripheral retina can be advantageous.

Various systems, methods and devices disclosed herein are directed towards intraocular lenses (IOLs) including, for example, posterior chamber IOLs, phakic IOLs and piggyback IOLs, which are configured to improve peripheral vision. For normal patients, e.g., uncomplicated cataract patients, peripheral vision may be balanced with good central vision in order to improve or maximize overall functional vision. For those patients having a pathological loss of central vision, peripheral vision may be improved or maximized for field angles 30-40 degrees with respect to the optic axis. For some patients, peripheral vision may be improved or maximized by taking into account the visual angle where the retina is healthy.

BRIEF DESCRIPTION OF THE DRAWINGS

The systems, methods and devices may be better understood from the following detailed description when read in conjunction with the accompanying schematic drawings, which are for illustrative purposes only. The drawings include the following figures.

DETAILED DESCRIPTION

Figure 1:
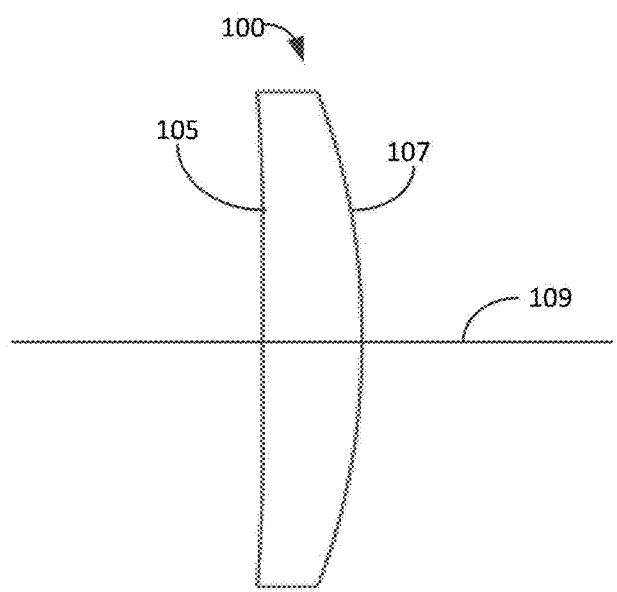
FIG. 1 illustrates an embodiment of a meniscus lens.

Patients suffering from AMD experience loss of central vision and rely on their peripheral vision to view objects in their environment. One way to aid patients with AMD currently is through the use of magnification. Magnification is usually accomplished by a high power loupe or telescope. Magnification can be achieved with implantable telescopes in one or both eyes. For example, a two-lens system can be employed to provide magnification for AMD patients. As another example, a lens system comprising a Lipshitz mirror telescope can be employed to provide magnification for AMD patients. However, the current solutions may not be configured to correct refractive errors at the fovea or at the peripheral retinal locations. Solutions for AMD patients can benefit from increasing visual quality at peripheral retinal location.

Glaucoma affects 2% of the population above age 40 and prevalence increases with age. Patients suffering from Glaucoma gradually lose peripheral vision as a result of damage to the optic nerve. As Glaucoma progresses, the central vision also gets affected. Glaucoma is usually diagnosed through a variety of methods including measuring intraocular pressure (IOP) and/or performing visual field tests (perimetry). Accordingly, IOLs visual field tests are configured to measure visual acuity for a variety of visual field angles between −30 degrees to 30 degrees. Patients suffering from Glaucoma gradually lose peripheral vision. Accordingly, Glaucoma patients can benefit from optical solutions that increase visual quality for peripheral vision.

Various IOLs that are currently available in the market while configured to provide good visual acuity for central vision can introduce refractive errors (e.g., defocus and/or astigmatism) in the peripheral vision. Accordingly, IOLs that can reduce peripheral refractive errors while also providing maintaining or increasing image quality at the fovea can be beneficial to patients with Glaucoma who may or may not suffer also from cataract. IOL designs that can reduce these peripheral refractive errors can have several benefits including but not limited to the following:

1. For patients at risk of Glaucoma, or who are being monitored for Glaucoma progression, reduced peripheral optical errors can make the visual field tests more sensitive to disease progression, which could otherwise be masked in the presence of peripheral optical errors (e.g., defocus) introduced by a standard IOL.
2. The extra contrast on the peripheral images that can result from IOLs with reduced peripheral optical errors can improve a Glaucoma patient's or an AMD patient's ability to perform tasks such as walking, reading, balance, risk of falling and driving.

Various IOL designs configured to improve peripheral image quality are described in U.S. application Ser. No. 14/692,609 filed on Apr. 21, 2015 published as U.S. Publication No. 2015/0320547 which is incorporated by reference here in its entirety. Various IOL designs configured to improve peripheral image quality for patients with AMD are described in U.S. application Ser. No. 14/644,101 (filed on Mar. 10, 2015, Published as U.S. Publication No. 2015/0265399); Ser. No. 14/644,110 (filed on Mar. 10, 2015, Published as U.S. Publication No. 2015/0297342); Ser. No. 14/644,107 (filed on Mar. 10, 2015, Published as U.S. Publication No. 2015/0297342); Ser. No. 14/849,369 (filed on Sep. 9, 2015) and Ser. No. 14/644,082 (filed on Mar. 10, 2015, Published as U.S. Publication No. 2015/0250583). Each of the above-identified application is incorporated by reference herein in its entirety.

Various embodiments of IOLs configured to improve image quality at one or more peripheral retinal locations can comprise at least one of redirection elements, refractive index gradient, multi-refraction elements, asymmetric Zernike surfaces or Fresnel diffractive elements. In various embodiments, the shape factor of the IOLs can be modified to correct errors in the peripheral retinal location. Furthermore, embodiments of IOLs configured to improve image quality at one or more peripheral retinal locations can b e both symmetric (improving the peripheral field in all locations) and asymmetric (improving the area around the PRL).

Various embodiments of IOLs configured to improve image quality at one or more peripheral retinal locations can comprise piggyback lenses that can improve peripheral MTF using thin and thick designs to reduce peripheral refractive errors, astigmatism, coma and other optical errors. Various embodiments of IOLs configured to improve image quality at one or more peripheral retinal locations can comprise toric, aspheric, higher order aspheric, Zernike and biconic surfaces, overlaid on either meniscus, biconvex or biconcave designs. Various embodiments of IOLs configured to improve image quality at one or more peripheral retinal locations can comprise piggyback lenses with Fresnel surfaces. In some embodiments, the principal plane of an existing IOL can be displaced to improve image quality at one or more peripheral retinal locations.

Embodiments of IOLs that are configured to improve image quality at one or more peripheral retinal locations can be configured to correcting astigmatism and coma that arise from oblique incidence. In addition to correcting astigmatism and coma arising from oblique incidence of light, it may be advantageous to provide embodiments of IOLs that can correct longitudinal chromatic aberrations to improve image quality at one or more peripheral retinal locations. Correcting longitudinal chromatic aberrations in addition to correcting astigmatism and coma that arise from oblique incidence of light can further improve image quality at peripheral retinal locations.

Various embodiments disclosed herein comprise an IOL including an achromatic optical element. For example, an IOL configured to correct peripheral aberrations through the use of shape factor, displacement and correct balancing of higher order aberrations can be combined with an achromatic optical element or an achromatic surface optimized for the power of the IOL. In various embodiments the achromatic surface can be disposed on the side of the IOL that has a lower slope. For example, in various embodiments, the achromatic surface can be disposed on the anterior side that is configured to receive incident light which may have a lower slope rather than the posterior side.

Various embodiments of IOLs disclosed herein are configured to correct peripheral refractive errors for visual field angles up to ±30-degrees. At least one of a shape factor, a placement of the IOL in the eye, curvature and/or asphericity of the surfaces of the IOL disclosed herein can be adjusted such that residual peripheral refractive errors for visual field angles up to ±30-degrees when the IOL is implanted in the eye is less than a threshold amount. Various embodiments of IOLs disclosed herein can include an achromatic optical element. For example, an IOL configured to correct peripheral aberrations through the use of shape factor, displacement and balancing of higher order aberrations can be combined with an achromatic optical element or an achromatic surface optimized for the power of the IOL.

Embodiments of IOLs with Double Asphere Design

Various embodiments of IOLs configured to improve image quality at one or more peripheral retinal locations can comprise a meniscus lens in which both the anterior and posterior surfaces are aspheric (also referred to as Double Asphere Design (DAD)). To improve the image quality at one or more peripheral retinal locations, the meniscus lens can be implanted such that the principal plane of the lens is displaced by an amount such as, for example about 0.2 mm and about 0.6 mm posteriorly from the iris as compared to the position where a standard intraocular lens (e.g., a meniscus IOL) is implanted. In various embodiments, the meniscus lens can have a negative shape factor, wherein the first surface is concave and the second surface is convex. To correct longitudinal chromatic aberrations, a meniscus lens having a first surface that is concave and a second surface that is convex can include an achromatic surface placed on the anterior part that is flatter (or has a lower slope) as compared to the posterior surface. The meniscus (e.g., double asphere design) lens including an achromatic surface can comprise:

a) a thickness greater than about 0.3 mm. For example, the thickness can be between about 0.5 mm and about 0.9 mm, between about 0.6 mm and about 1.0 mm, between about 0.7 mm and about 1.2 mm, between about 0.8 mm and about 1.3 mm, between about 0.9 mm and about 1.4 mm, between about 1.1 mm and about 1.5 mm, between about 1.2 mm and about 1.6 mm. The optical performance of a thicker lens can be better than the optical performance of a thinner lens. However, a thicker lens can require larger incisions for implantation.

b) a shape factor between about −1 (corresponding to a planoconvex lens) and about −3. In addition, the curvature of the anterior surface of the IOL comprising a meniscus design can be configured to be sensitive to eccentricity, as well as enhance optical performance.

Embodiments of IOLs with Biconvex Design

Various embodiments of IOLs configured to improve image quality at one or more peripheral retinal locations can comprise a biconvex design (also referred to as BOSS herein) in which both the anterior and the posterior surfaces have similar curvatures. The anterior and the posterior surfaces can be aspheric. In various embodiments, embodiments of IOL having biconvex lens designs can be implanted such that the principal plane of the lens is displaced by an amount such as, for example about 0.5 mm and about 1.0 mm posteriorly from the iris as compared to the position where a standard IOL (e.g., a biconvex lens design) is implanted. The biconvex lens can have a shape factor close to zero, and a thickness between about 0.7 mm and about 1.0 mm. In various embodiments of IOLs with biconvex design, the achromatic surface can be placed on the anterior side or the posterior side, since both the anterior and posterior surface can have similar curvature in most practical implementations.

Various embodiments of biconvex lens designs are illustrated in FIGS. 35-38 in U.S. Publication No. 2015/0320547A1 which is incorporated by reference herein in its entirety herein for all that it discloses.

The achromatic optical element or surface integrated with the meniscus lens design (e.g., double aspheric design) or the biconvex lens design can comprise:

1) An add power that can correct the chromatic aberration of the eye. For example, for an IOL having 20 Diopter power can have an add power of about 3.5 Diopter to correct for chromatic aberration.
2) A step height of k=−1 if the achromatic optical element or surface is on the anterior side and a step height k=1 on the posterior side. In various embodiments, the achromatic optical element or surface can be monofocal. Although, other variations are possible.
3) The achromatic optical element or surface can be designed for a wavelength of 550 nm. Although, other variations are possible.

Embodiments of IOLs with an Achromat

FIG. 1 illustrates an embodiment of a meniscus IOL 100 that is configured to be implanted in the eye of a patient. The IOL 100 has an anterior surface 105 and a posterior surface 107 opposite the anterior surface. The anterior and the posterior surface are intersected by an optical axis 109. The thickness of the IOL 100 along the optical axis 109 can be between about 0.7 mm and about 1.4 mm. For example, the thickness of the IOL 100 along the optical axis 109 can be between about 0.8 mm and about 1.3 mm. between about 0.9 mm and about 1.2 mm, between about 1.0 mm and about 1.1 mm, or any value in between these values. The IOL 100 can be configured to improve image quality at one or more locations of the peripheral retinal through the use of shape factor, displacement of the principal plane and correction of higher order aberrations.

It is noted from FIG. 1, that the anterior surface 105 of the IOL 100 is nearly flat. Furthermore, the anterior surface 105 has a curvature (or slope) that is less than a curvature (or slope) of the posterior surface 107. An IOL having an anterior surface 105 that is nearly flat can have several benefits. For example, an anterior surface that is nearly flat can be less sensitive to eccentricity between anterior and posterior surfaces. As another example, a nearly flat anterior surface can make the addition of an achromatic element or surface to function more effectively.

Figure 2:
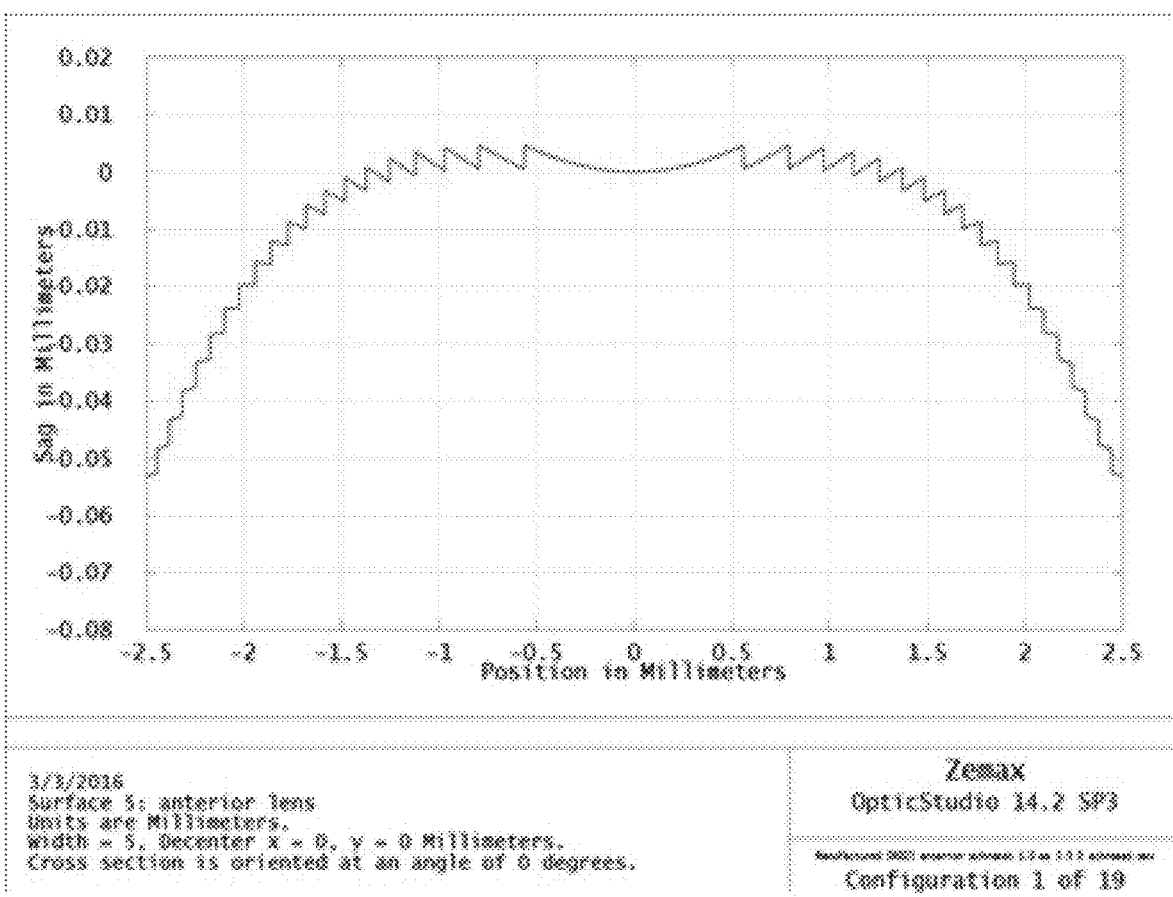
FIG. 2 illustrates a portion of an achromatic element integrated with an anterior surface of the embodiment of the meniscus lens depicted in FIG. 1.

FIG. 2 illustrates a portion of an achromatic element integrated with an anterior surface of the embodiment of the meniscus lens depicted in FIG. 1. As discussed above, an achromatic element having a surface profile as depicted in FIG. 2 can be combined with an IOL similar to the IOL 100 depicted in FIG. 1 to improve image quality in one or more peripheral retinal locations. In various embodiments the achromatic element can be disposed on the side of the IOL that has a lower slope. For example, the achromatic element having a surface profile as depicted in FIG. 2 can be disposed on the nearly flat anterior surface 105 of the embodiments of the IOL 100 depicted in FIG. 1.

Figure 3:
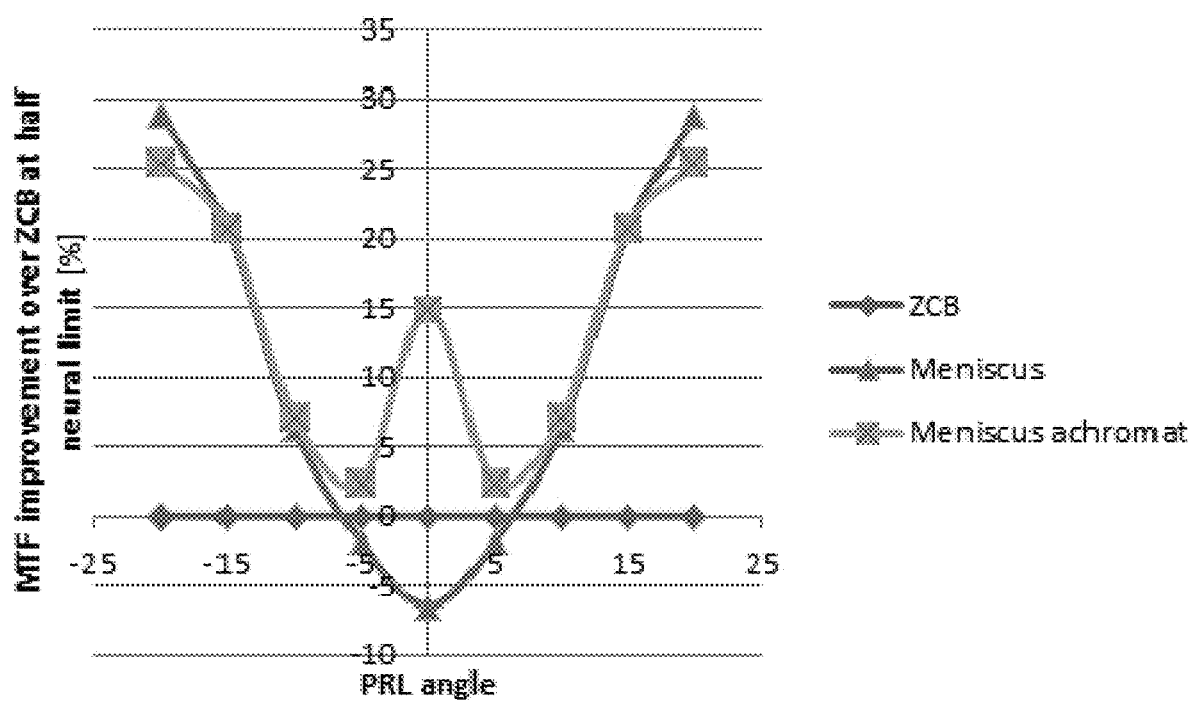
FIG. 3 illustrates performance of a meniscus lens comprising an achromatic element, a meniscus lens without an achromatic element and a standard intraocular lens (ZCB).

FIG. 3 illustrates the percentage modulus of the optical transfer function (MTF) improvement over the a standard intraocular lens (ZCB) at half the neural limit spatial frequency as a function of the angle of the peripheral retinal location with respect to the optical axis for a meniscus lens comprising an achromatic element and a meniscus lens without an achromatic element. The peripheral retinal location can have an eccentricity between −60 degrees and 60 degrees with respect to the optical axis. In various implementations, the peripheral retinal location can have an eccentricity between about −45 degrees and 45 degrees, between about −30 degrees and 30 degrees, between about −25 degrees and 25 degrees, or values therebetween. The angular ranges for eccentricity of the peripheral retinal location refer to the visual field angle in object space between an object with a corresponding retinal image on the fovea and an object with a corresponding retinal image on a peripheral retinal location. It can be seen that adding the achromat substantially improves the contrast in the central region, which is beneficial for patients maintaining some residues of central visual performance, while simultaneously keeping the good peripheral performance for the meniscus lens design with an achromat.

In various embodiments, the achromatic optical element or achromatic surface can be disposed on the less curved side. As discussed above, an advantage of introducing the achromatic optical element or achromatic surface comes from improved central visual performance, while still maintaining the good peripheral vision. The advantage of disposing the achromatic optical element or the achromatic surface on the less curved surface is observed from the figures below.

Figure 4A:
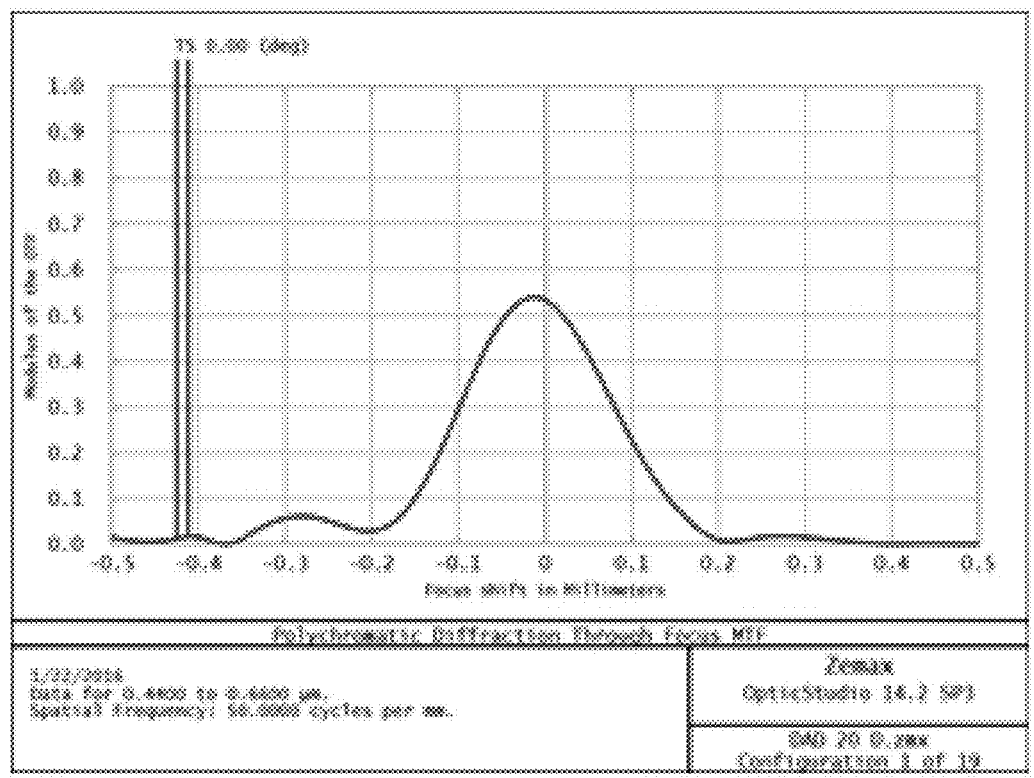
FIG. 4A illustrates a central polychromatic MTF for a meniscus lens without an achromatic element.
Figure 4B:
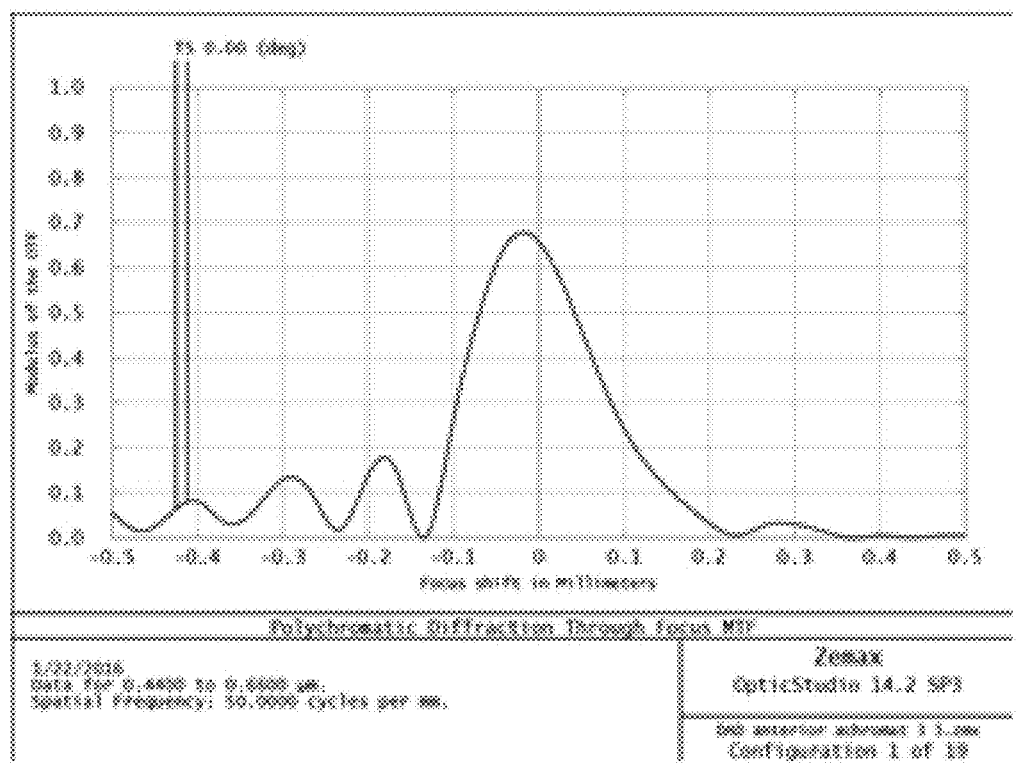
FIG. 4B illustrates a central polychromatic MTF for a meniscus lens having an achromatic element integrated with the anterior surface of the meniscus lens.

FIG. 4A illustrates polychromatic MTF for a meniscus lens without an achromatic element at the fovea. FIG. 4B illustrates polychromatic MTF for a meniscus lens having an achromatic element integrated with the anterior surface of the meniscus lens at the fovea.

Figure 5A:
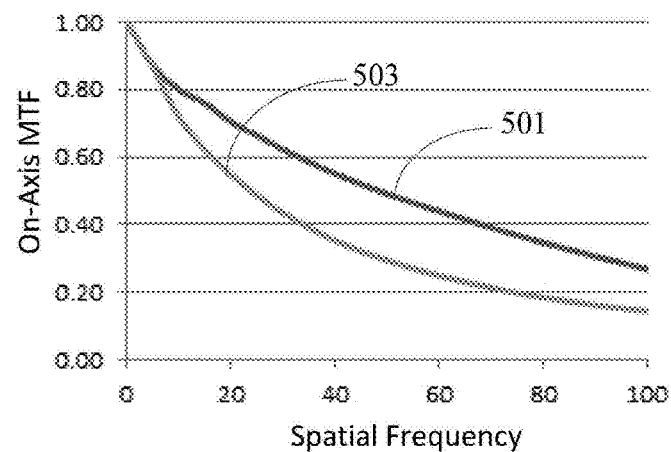
FIG. 5A illustrates on-axis MTF versus spatial frequency for a 5 mm pupil in polychromatic light for a double aspheric lens having an achromatic element integrated with its anterior surface and a double aspheric lens without an achromatic element

Several lenses according to the above described principles were manufactured and their performance measured in physical eye models. Examples of measured performance are depicted in FIGS. 5A-8B. FIG. 5A illustrates on-axis MTF versus spatial frequency for a 5 mm pupil in polychromatic light for a double aspheric lens (e.g, both the posterior and anterior surfaces are aspheric) having an achromatic element integrated with its anterior surface (curve 501) and a double aspheric lens without an achromatic element (curve 503). The on-axis MTF for double aspheric lens with an achromatic optical element disposed on the anterior surface is greater than the corresponding on-axis MTF for double aspheric lens without an achromatic optical element for spatial frequency greater than 20 cycles/mm indicating improved foveal vision for the double aspheric lens with an achromatic optical element disposed on the anterior surface as compared to the double aspheric lens without an achromatic optical element.

Figure 5B:
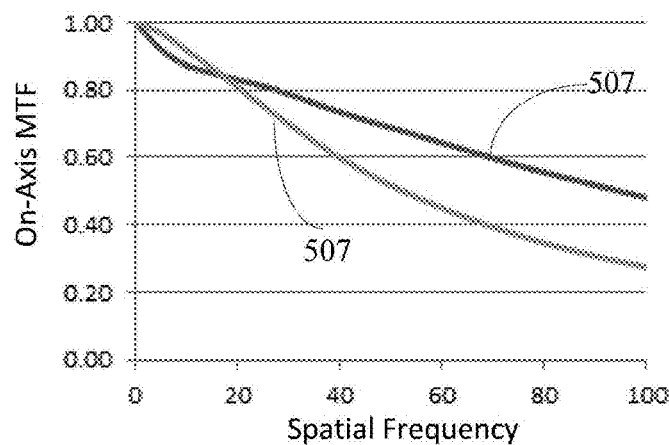
FIG. 5B illustrates on-axis MTF versus spatial frequency for a 3 mm pupil in polychromatic light a double aspheric lens having an achromatic element integrated with its anterior surface and a double aspheric lens without an achromatic element.
Figure 6A:
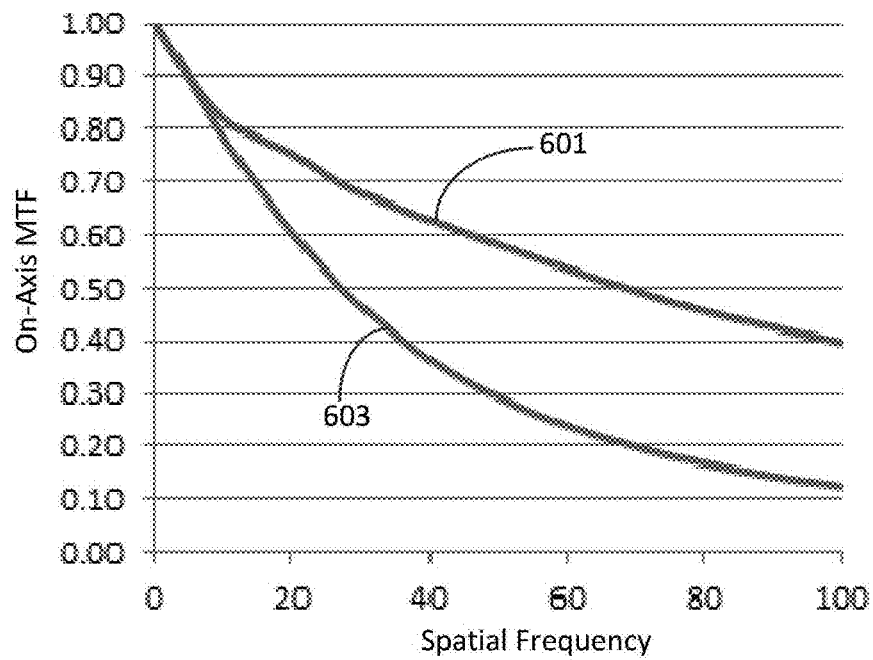
FIG. 6A illustrates on-axis MTF versus spatial frequency for a 5 mm pupil in polychromatic light for a biconvex lens having an achromatic element integrated with its anterior surface and a biconvex lens without an achromatic element.
Figure 6B:
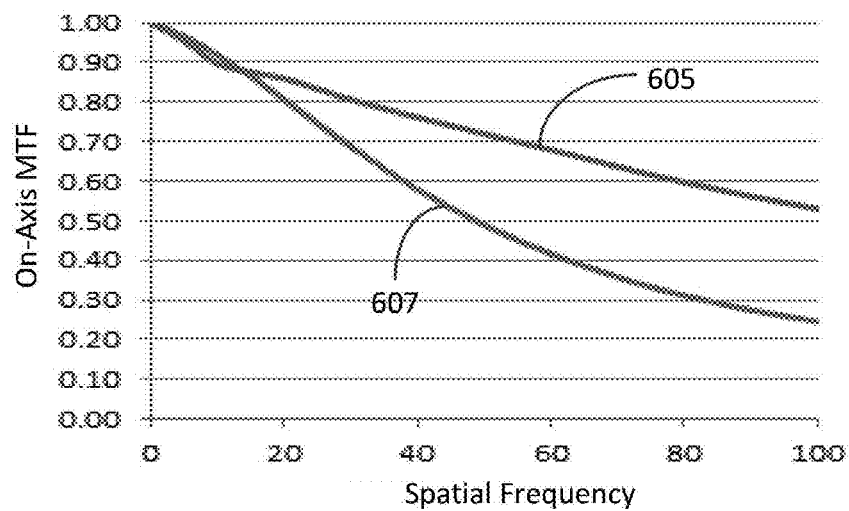
FIG. 6B illustrates on-axis MTF versus spatial frequency for a 3 mm pupil in polychromatic light a biconvex lens having an achromatic element integrated with its anterior surface and a biconvex lens without an achromatic element.

FIG. 5B illustrates on-axis MTF versus spatial frequency for a 3 mm pupil in polychromatic light a double aspheric lens having an achromatic element integrated with its anterior surface (curve 505) and a double aspheric lens without an achromatic element (curve 507). Similar to the 5 mm pupil condition, the on-axis MTF for double aspheric lens with an achromatic optical element disposed on the anterior surface is greater than the corresponding on-axis MTF for double aspheric lens without an achromatic optical element for spatial frequency greater than 20 cycles/mm indicating improved foveal vision for the double aspheric lens with an achromatic optical element disposed on the anterior surface as compared to the double aspheric lens without an achromatic optical element. Similar measurements are performed with a biconvex design (BOSS) in which the anterior and posterior surfaces have approximate similar curvatures, which are shown below in FIGS. 6A and 6B. With reference to FIGS. 6A and 6B, curves 601 and 605 on-axis MTF versus spatial frequency for a 5 mm pupil and 3 mm pupil respectively in polychromatic light for a biconvex lens having an achromatic element integrated with its anterior surface. With reference to FIGS. 6A and 6B, curves 603 and 607 on-axis MTF versus spatial frequency for a 5 mm pupil and 3 mm pupil respectively in polychromatic light for a biconvex lens without an achromatic element. It is noted that on-axis MTF for a biconvex lens with an achromatic optical element disposed on the anterior surface is greater than the corresponding on-axis MTF for a biconvex lens without an achromatic optical element for spatial frequency greater than 20 cycles/mm for both 5 mm and 3 mm pupil indicating improved foveal vision for the biconvex lens with an achromatic optical element disposed on the anterior surface as compared to the biconvex lens without an achromatic optical element.

Figure 7A:
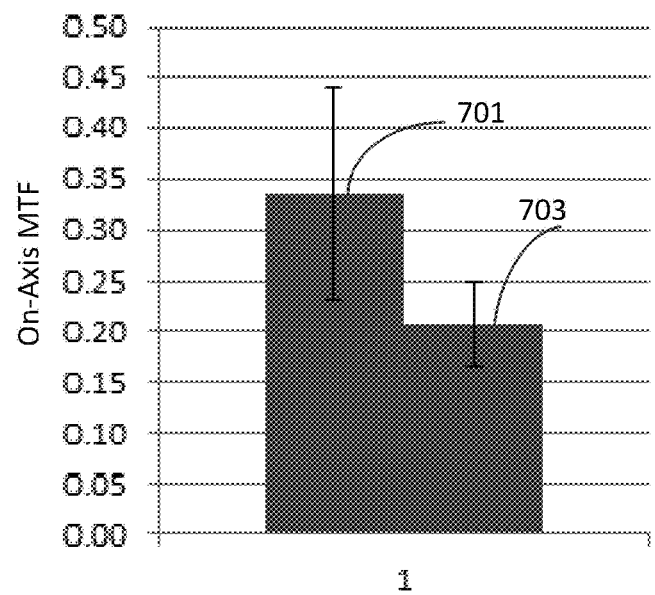
FIG. 7A illustrates on-axis MTF for a spatial frequency of 50 cycles/mm for a 5 mm pupil in polychromatic light for a meniscus lens comprising an achromatic element and a meniscus lens without an achromatic element.
Figure 7B:
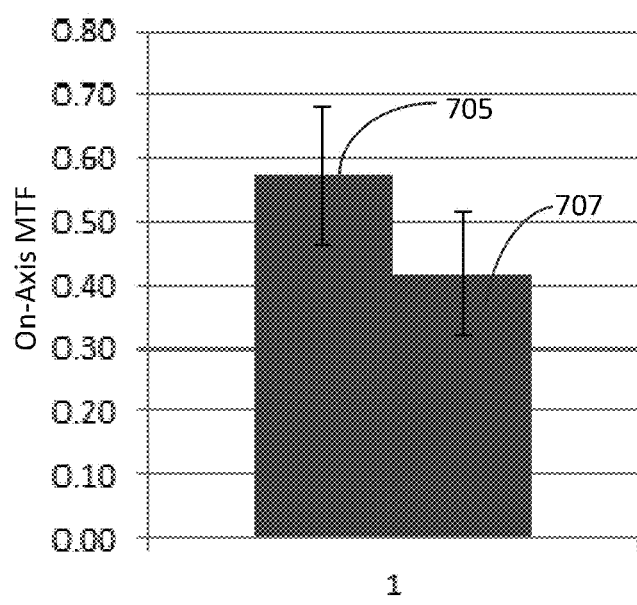
FIG. 7B illustrates on-axis MTF for a spatial frequency of 50 cycles/mm for a 3 mm pupil in polychromatic light for a meniscus lens comprising an achromatic element and a meniscus lens without an achromatic element.

It is noted that for both 3 mm pupil condition and 5 mm pupil condition, the achromat optical element enhances optical performance for spatial frequencies above 50 cycles per mm, which is often used to illustrate on-axis performance. The on-axis best focus MTF for a spatial frequency of 50 cycles/mm for the meniscus lens with and without achromat optical element for 5 mm pupil condition and 3 mm pupil condition is shown in FIGS. 7A and 7B respectively. Referring to FIG. 7A, block 701 illustrates the on-axis best focus MTF for a spatial frequency of 50 cycles/mm for the meniscus lens with an achromat optical element for the 5 mm pupil condition and block 703 illustrates the on-axis best focus MTF for a spatial frequency of 50 cycles/mm for the meniscus lens without an achromat optical element for the 5 mm pupil condition. Referring to FIG. 7B, block 705 illustrates the on-axis best focus MTF for a spatial frequency of 50 cycles/mm for the meniscus lens with an achromat optical element for the 3 mm pupil condition and block 707 illustrates the on-axis best focus MTF for a spatial frequency of 50 cycles/mm for the meniscus lens without an achromat optical element for the 3 mm pupil condition. It is noted that for both pupil conditions, the optical performance for the meniscus lens with achromatic optical element is better than the optical performance for the meniscus lens without achromatic optical element.

Figure 8A:
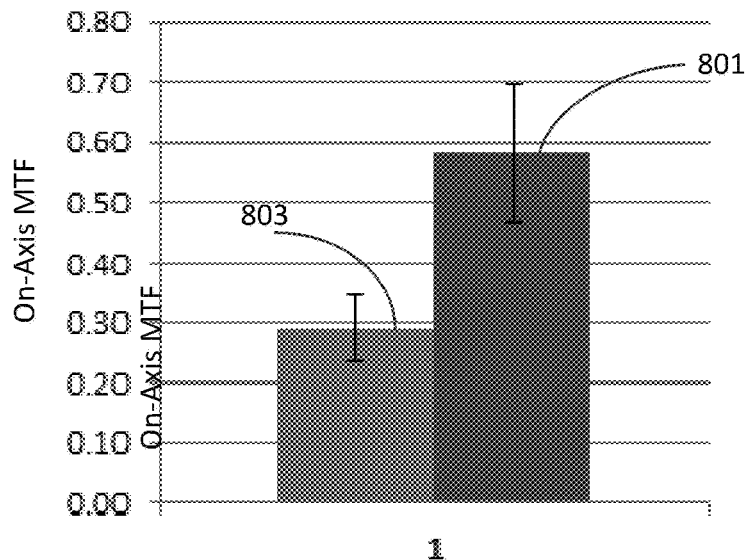
FIG. 8A illustrates on-axis MTF for a spatial frequency of 50 cycles/mm for a 5 mm pupil in polychromatic light for a biconvex lens comprising an achromatic element and a biconvex lens without an achromatic element.
Figure 8B:
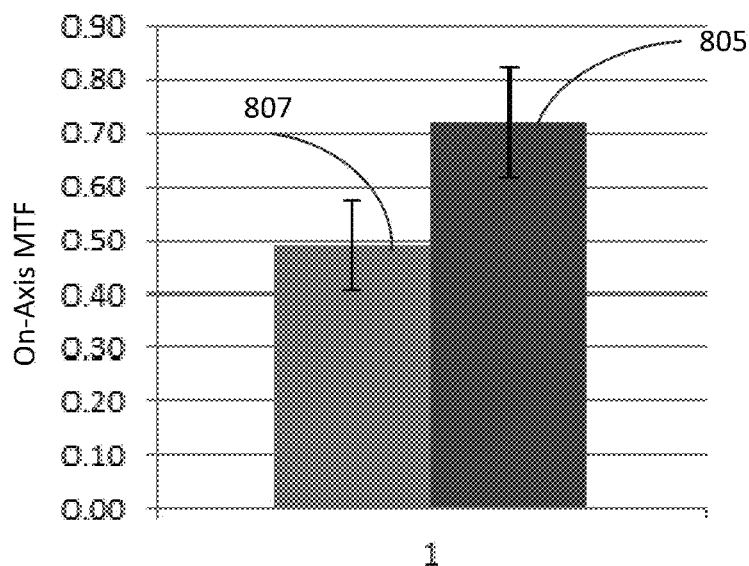
FIG. 8B illustrates on-axis MTF for a spatial frequency of 50 cycles/mm for a 3 mm pupil in polychromatic light for a biconvex lens comprising an achromatic element and a biconvex lens without an achromatic element.

FIG. 8A illustrates on-axis MTF for a spatial frequency of 50 cycles/mm for a 5 mm pupil in polychromatic light for a biconvex lens comprising an achromatic element (block 801) and a biconvex lens without an achromatic element (block 803). FIG. 8B illustrates on-axis MTF for a spatial frequency of 50 cycles/mm for a 3 mm pupil in polychromatic light for a biconvex lens comprising an achromatic element (block 805) and a biconvex lens without an achromatic element (block 807). It is noted that for both pupil conditions, the optical performance for the biconvex lens with achromatic optical element is better than the optical performance for the biconvex lens without achromatic optical element.

In addition to substantial reduction in off-axis aberrations, such as, for example, oblique astigmatism, the surface geometries of the anterior and posteriors surfaces of the Double Aspheric Design (DAD) IOL can be configured to maintain on-axis image quality similar to existing monofocal IOLs that are configured to provide foveal vision. Various embodiments of IOLs (e.g., DAD IOLs) described herein can have a central axial thickness that is greater than the central axial thickness of existing monofocal IOLs that are configured to provide foveal vision. For example, various embodiments of IOLs described herein can have a central thickness of about 1.2 mm. As another example, various embodiments of IOLs described herein can have a central thickness greater than 0.5 mm and less than 2.0 mm, greater than or equal to about 0.6 mm and less than or equal to about 1.9 mm, greater than or equal to about 0.7 mm and less than or equal to about 1.8 mm, greater than or equal to about 0.9 mm and less than or equal to about 1.7 mm, greater than or equal to about 1.0 mm and less than or equal to about 1.6 mm, greater than or equal to about 1.1 mm and less than or equal to about 1.5 mm, greater than or equal to about 1.2 mm and less than or equal to about 1.4 mm, or any value in these ranges/sub-ranges. Various embodiments of the IOLs discussed herein (e.g., DAD IOL) can be vaulted when placed in the eye of the patient. For example, various embodiments of IOLs described herein can be vaulted by about 0.2 mm towards the retina as compared to existing monofocal IOLs that are configured to provide foveal vision. As another example, various embodiments of IOLs described herein can be vaulted towards the retina by an distance between about 0 mm and about 1.5 mm as compared to existing monofocal IOLs that are configured to provide foveal vision. The vault distance can be greater than or equal to about 0.05 mm and less than or equal to about 1.5 mm, greater than or equal to about 0.1 mm and less than or equal to about 1.4 mm, greater than or equal to about 0.2 mm and less than or equal to about 1.3 mm, greater than or equal to about 0.5 mm and less than or equal to about 1.2 mm, greater than or equal to about 0.75 mm and less than or equal to about 1.0 mm, or any value in these ranges/sub-ranges.

Various embodiments of DAD IOLs that can be used for cataract patients with or at risk for Age-related Macular Degeneration (AMD) and/or Glaucoma can comprise aspheric anterior and posterior surfaces. Various embodiments of DAD IOLs contemplated herein can be configured to provide good optical quality at the fovea as well at a location of the peripheral retina. Good optical quality at the location of the peripheral retina can be achieved by optimizing the surface geometries of the anterior and posterior surfaces of the IOL, by adjusting the central axial thickness of the IOL and/or by optimizing the distance of the anterior surface of the IOL from the iris. Currently, about 10% of patients undergoing cataract surgery have some form of AMD. Patients with AMD eventually lose their central vision, leaving only their peripheral vision. Therefore, IOLs configured to provide high image quality in the peripheral visual field, while simultaneously maintaining sufficient contrast ratio for central vision (also referred to herein as foveal vision), so that any remaining central vision can be used as long as possible are desirable. However, IOLs available commercially can exacerbate peripheral optical errors. Since patients with AMD can have their vision improved by correction of optical errors in the periphery, correction of peripheral optical errors represent an area of potentially improved visual quality of life.

Without subscribing to any particular theory, the anterior and posterior surface sag Z of various embodiments of DAD IOLs can be obtained from equation (1):

$$z = \frac{cr^2}{1 + \sqrt{1-(k+1)c^2r^2}} + a_4 r^4 + a_6 r^6 + a_8 r^8 + a_{10} r^{10} \qquad (1)$$

where r is the radial distance from the center of the lens, c is the curvature, k is the conic constant and a4, a6, a8, and a10 are the higher order aspheric terms.

The values of the central thickness and vault height for various embodiments of DAD IOLs can be selected keeping in view the following factors: (i) optical performance—IOLs with increased central thickness and higher vault height have increased optical performance; (ii) mechanical stability—which places an upper limit on vault height; (iii) ease of insertion in a human eye—smaller incision size (e.g., about 2.8 mm) is desirable which places a condition on central thickness; and (iv) functional optical zone size—increased central thickness of the IOL can provide an increase functional optical zone, which can desirable for AMD patients, many of who exhibit enlarged pupils. An example embodiment of a DAD IOL optimized based on the factors discussed above can have a vault height of about 0.45 mm, a central thickness of 1.2 mm and a functional optic zone of about 6 mm. Another example of a DAD IOL optimized to provide good foveal as well as peripheral visual quality can have a vault height between about 0.05 mm and about 1.5 mm, a central thickness between about 0.7 mm and about 1.5 mm and a functional optic zone having a size between about 4.5 mm and about 6.5 mm (e.g., a functional optic zone having a size of about 5 mm, or a functional optic zone having a size of about 6 mm).

Table 1 below provides the values of the coefficients that define the anterior and posterior surface of various embodiments of DAD IOLs having optical power from about 18 D to about 30 D. In Table 1, column A is the optical power in Diopters for various embodiments of the DAD IOL, column B indicates one of an anterior (Ant.) or a posterior (Post.) surface for various embodiment of the DAD IOL, column C is the central thickness in mm for various embodiment of the DAD IOL, column D is the vault height (towards the retina) in mm for various embodiment of the DAD IOL, column E is the radius of curvature of the respective surface (Ant. Or Post.) for various embodiment of the DAD IOL, column F is the conic constant k used to design the respective surface (Ant. Or Post.) for various embodiment of the DAD IOL, columns G, H and I are the higher order aspheric terms $a_4$, $a_6$, $a_8$ and $a_{10}$ used to design the respective surface (Ant. Or Post.) for various embodiment of the DAD IOL. For any given optical power, it is envisioned that specific embodiments include variations in any value in columns C through J of up to about 15%, or preferably up to about 10%, or up to about 5%. In specific embodiments, the range of optical powers can be between 5D and 40D, or preferably between from about 18D to about 30D, or between about 21D and about 27D.

Figure 9A:
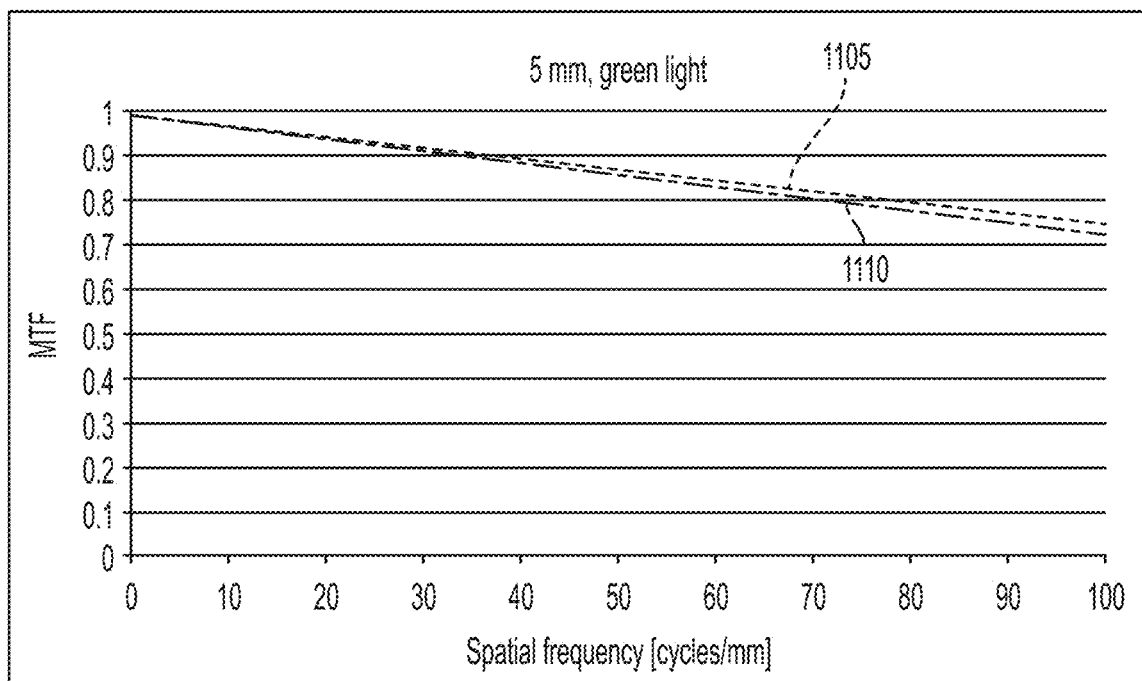
FIGS. 9A and 9B illustrate simulated on-axis modulus transfer function (MTF) for different embodiments of an IOL with a 5 mm entrance pupil for green and white light respectively.
Figure 9B:
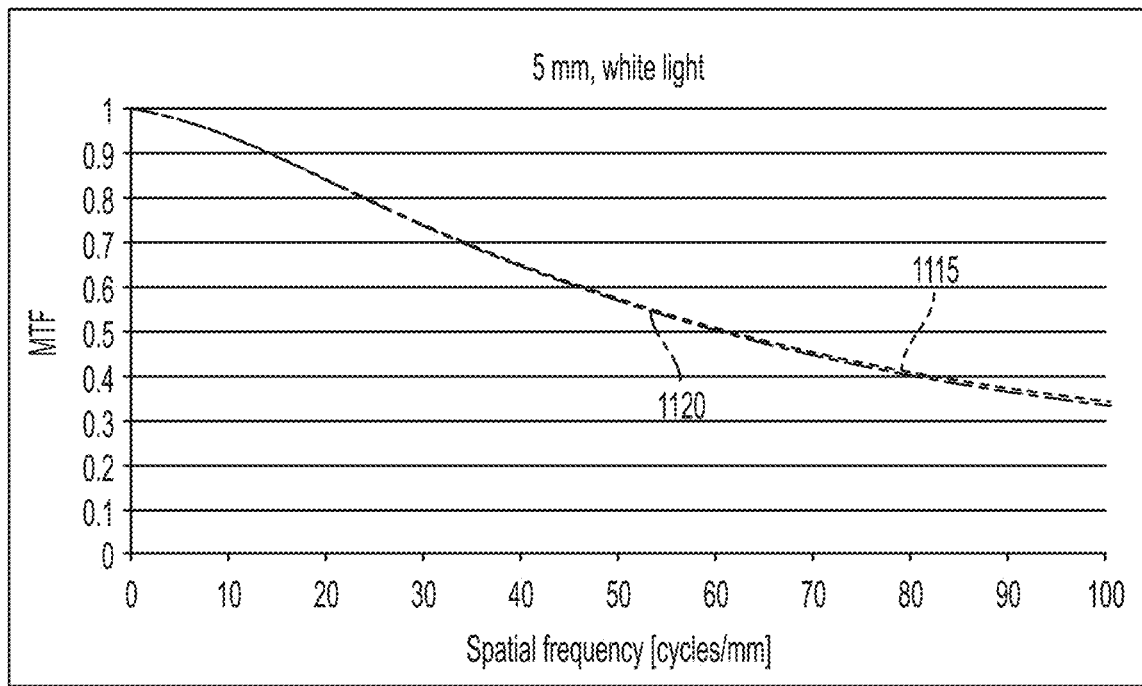

FIGS. 9A and 9B illustrate the comparison of on-axis modulus transfer function (MTF) for an embodiment of the DAD IOL and an embodiment of an existing monofocal IOL (referred to herein as ZCB) that is configured to provide good on-axis image quality. The on-axis MTF was obtained with a 5 mm entrance pupil for green and white light respectively. Referring to FIG. 9A, curve 1105 illustrates the on-axis MTF for the ZCB lens and curve 1110 illustrates the on-axis MTF for the embodiment of the DAD IOL. Referring to FIG. 9B, curve 1115 illustrates the on-axis MTF for the ZCB lens and curve 1120 illustrates the on-axis MTF for the embodiment of the redesigned DAD IOL. The on-axis MTF performance of the embodiment of the DAD IOL is

TABLE 1

Coefficients for Various Embodiments of DAD IOLs

| A | B | C | D | E | F | G | H | I | J |
|---|---|---|---|---|---|---|---|---|---|
| 18 | Ant | 1.2 | 0.45 | −34.0000 | 62.3719 | −0.0027 | 0.0002 | −3.2960E−05 | 1.3656E−06 |
|  | Post |  |  |  | −6.0674 | −0.3732 | −0.0011 | 9.5254E−05 | −2.8723E−05 | 1.5611E−06 |
| 18.5 | Ant | 1.2 | 0.45 | −39.0000 | 85.8619 | −0.0026 | 0.0002 | −2.8652E−05 | 1.2215E−06 |
|  | Post |  |  |  | −6.0674 | −0.3732 | −0.0011 | 9.5254E−05 | −2.8723E−05 | 1.5611E−06 |
| 19 | Ant | 1.2 | 0.45 | −46.3000 | 22.6898 | −0.0030 | 0.0003 | −4.73840E−05 | 2.3728E−06 |
|  | Post |  |  |  | −6.0674 | −0.3732 | −0.0011 | 9.5254E−05 | −2.8723E−05 | 1.5611E−06 |
| 19.5 | Ant | 1.2 | 0.45 | −57.7272 | 22.6898 | −0.0030 | 0.0002 | −4.8136E−05 | 2.6297E−06 |
|  | Post |  |  |  | −6.0674 | −0.3732 | −0.0011 | 9.5254E−05 | −2.8723E−05 | 1.5611E−06 |
| 20 | Ant | 1.2 | 0.45 | −70.0202 | −268.2743 | −0.0027 | 0.0001 | −2.8821E−05 | 1.6783E−06 |
|  | Post |  |  |  | −6.0674 | −0.3732 | −0.0011 | 9.5254E−05 | −2.8723E−05 | 1.5611E−06 |
| 20.5 | Ant | 1.2 | 0.45 | −99.9122 | −202.2094 | −0.0029 | 0.0002 | −4.8480E−05 | 2.8376E−06 |
|  | Post |  |  |  | −6.0674 | −0.3732 | −0.0011 | 9.5254E−05 | −2.8723E−05 | 1.5611E−06 |
| 21 | Ant | 1.2 | 0.45 | −152.2270 | −3,788.9704 | −0.0029 | 0.0002 | −4.1319E−05 | 2.4682E−06 |
|  | Post |  |  |  | −6.0674 | −0.3732 | −0.0011 | 9.5254E−05 | −2.8723E−05 | 1.5611E−06 |
| 21.5 | Ant | 1.2 | 0.45 | −182.0091 | −361,647.6159 | −0.0033 | 0.0003 | −5.8355E−05 | 3.3282E−06 |
|  | Post |  |  |  | −6.0674 | −0.3732 | −0.0011 | 9.5254E−05 | −2.8723E−05 | 1.5611E−06 |
| 22 | Ant | 1.2 | 0.45 | 1,400.8132 | 499.9714 | −0.0028 | 0.0002 | −4.912E−05 | 3.0176E−06 |
|  | Post |  |  |  | −6.0674 | −0.3732 | −0.0011 | 9.5254E−05 | −2.8723E−05 | 1.5611E−06 |
| 22.5 | Ant | 1.2 | 0.45 | 234.7048 | 499.9714 | −0.0025 | 0.0001 | −3.9724E−05 | 2.5863E−06 |
|  | Post |  |  |  | −6.0674 | −0.3732 | −0.0011 | 9.5254E−05 | −2.8723E−05 | 1.5611E−06 |
| 23 | Ant | 1.2 | 0.45 | 119.6339 | 542.8327 | −0.0027 | 0.0002 | −4.2923E−05 | 2.7471E−06 |
|  | Post |  |  |  | −6.0674 | −0.3732 | −0.0011 | 9.5254E−05 | −2.8723E−05 | 1.5611E−06 |
| 23.5 | Ant | 1.2 | 0.45 | 75.7704 | 222.3910 | −0.0028 | 0.0002 | −4.1273E−05 | 2.5735E−06 |
|  | Post |  |  |  | −6.0674 | −0.3732 | −0.0011 | 9.5254E−05 | −2.8723E−05 | 1.5611E−06 |
| 24 | Ant | 1.2 | 0.45 | 64.0352 | 26.5595 | −0.0025 | 0.00012 | −3.8891E−05 | 2.7603E−06 |
|  | Post |  |  |  | −6.0674 | −0.3732 | −0.0011 | 9.5254E−05 | −2.8723E−05 | 1.5611E−06 |
| 24.5 | Ant | 1.2 | 0.45 | 56.3231 | 325 | −0.0020 | −9.966E−05 | −2.4244E−05 | 2.75546E−06 |
|  | Post |  |  |  | −6.0625 | −0.3735 | −0.0011 | 9.5284E−05 | −2.8718E−05 | 1.5621E−06 |
| 25.5 | Ant | 1.2 | 0.45 | 42.0000 | 175.8434 | −0.0010 | 3.8248E−05 | −6.134E−05 | 4.1504E−06 |
|  | Post |  |  |  | −5.9553 | −1.6110 | 0.0003 | −1.3304E−05 | −4.5210E−05 | 3.0716E−06 |
| 26 | Ant | 1.2 | 0.45 | 42.0000 | 176.9004 | −0.0015 | 3.6653E−05 | −6.0126E−05 | 3.7168E−06 |
|  | Post |  |  |  | −5.8051 | −1.7452 | −0.0003 | −3.1379E−05 | −4.0827E−05 | 2.3503E−06 |
| 26.5 | Ant | 1.2 | 0.45 | 42.0000 | 165 | −0.0007 | −3.8090E−05 | −7.3157E−05 | 5.4138E−06 |
|  | Post |  |  |  | −5.6959 | −2.1823 | −0.0001 | −6.2260E−05 | −4.9226E−05 | 3.1986E−06 |
| 27 | Ant | 1.2 | 0.45 | 42.0000 | 190.8861 | 0.0001 | −0.0001 | −7.5315E−05 | 5.6927E−06 |
|  | Post |  |  |  | −5.5694 | −3.0004 | 0.0002 | −0.0002 | −4.9516E−05 | 3.7093E−06 |
| 27.5 | Ant | 1.2 | 0.45 | 42.0000 | 180 | 0.0029 | −0.0010 | 3.6918E−05 | 4.0249E−07 |
|  | Post |  |  |  | −5.4228 | −9.6203 | −0.0016 | −0.0005 | 2.5112E−05 | −2.9276E−07 |
| 28 | Ant | 1.2 | 0.45 | 17.0000 | 29.8 | −0.0003 | −0.0003 | −6.9101E−06 | 5.0698E−07 |
|  | Post |  |  |  | −6.6554 | −3.6216 | 3.0171E−05 | 3.6950E−05 | −4.5579E−05 | 3.5767E−06 |
| 28.5 | Ant | 1.2 | 0.45 | 17.0000 | 30.6721 | −0.0016 | −0.0002 | −1.4514E−05 | 3.0153E−07 |
|  | Post |  |  |  | −6.4311 | −2.0869 | −0.0003 | 3.0507E−05 | −4.4056E−05 | 3.1068E−06 |
| 29 | Ant | 1.2 | 0.45 | 17.0000 | 30.8740 | −0.0004 | −0.0003 | 8.9162E−07 | −2.3361E−07 |
|  | Post |  |  |  | −6.2959 | −2.4389 | 0.0008 | −0.0002 | −9.8752E−06 | 1.6458E−06 |
| 29.5 | Ant | 1.2 | 0.45 | 16.2100 | 27.7786 | −0.0014 | −0.0002 | −5.5401E−06 | −5.3526E−07 |
|  | Post |  |  |  | −6.2071 | −2.3782 | −0.0001 | −1.7481E−05 | −3.5970E−05 | 2.5057E−06 |
| 30 | Ant | 1.2 | 0.45 | 15.0196 | 23.6439 | −0.0006 | −0.0002 | −5.6338E−06 | −5.4174E−07 |
|  | Post |  |  |  | −6.2373 | −3.6459 | 0.0003 | −2.6967E−05 | −4.2032E−05 | 3.3649E−06 |

The performance of an embodiment of a DAD IOL is compared with an existing monofocal IOL that is configured to provide good on-axis image quality. The comparison of the performance of the embodiment of the DAD IOL and the existing monofocal IOL was based on the following three metrics: on-axis MTF, off-axis astigmatism and simulated peripheral VA.

comparable (e.g., substantially identical) to the on-axis MTF performance of the ZCB lens.

Figure 10A:
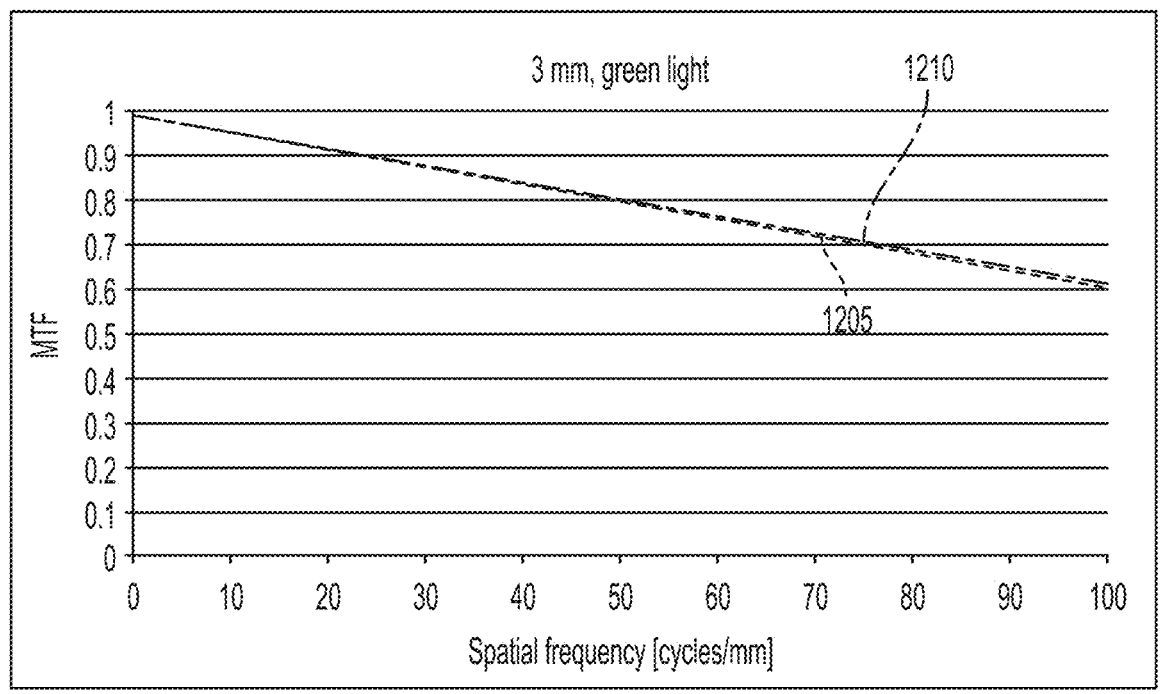
FIGS. 10A and 10B illustrate simulated on-axis modulus transfer function (MTF) for different embodiments of an IOL with a 3 mm entrance pupil for green and white light respectively.
Figure 10B:
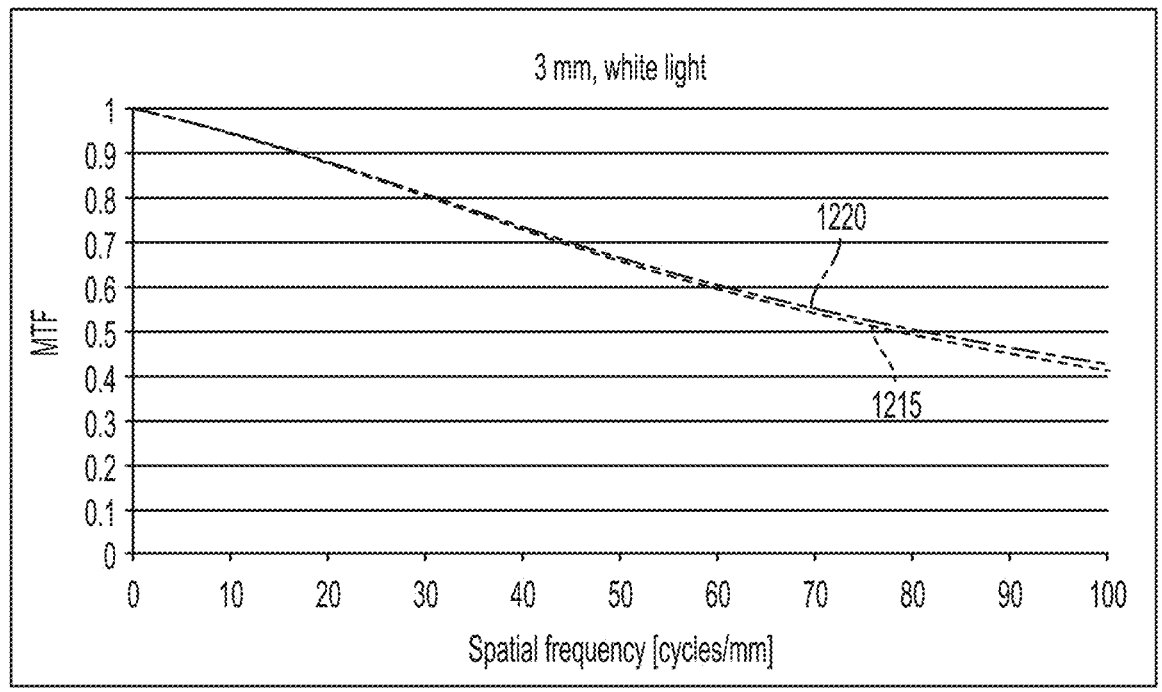

FIGS. 10A and 10B illustrate the comparison of on-axis modulus transfer function (MTF) for an embodiment of the DAD IOL and the ZCB lens. The on-axis MTF was obtained with a 3 mm entrance pupil for green and white light respectively. Referring to FIG. 10A, curve 1205 illustrates the on-axis MTF for the ZCB lens and curve 1210 illustrates the on-axis MTF for the DAD IOL. Referring to FIG. 10B, curve 1215 illustrates the on-axis MTF for the ZCB lens and curve 1220 illustrates the on-axis MTF for the DAD IOL. The on-axis MTF performance of the embodiment of DAD IOL is comparable (e.g., substantially identical) to the on-axis MTF performance of the ZCB lens.

Figure 11A:
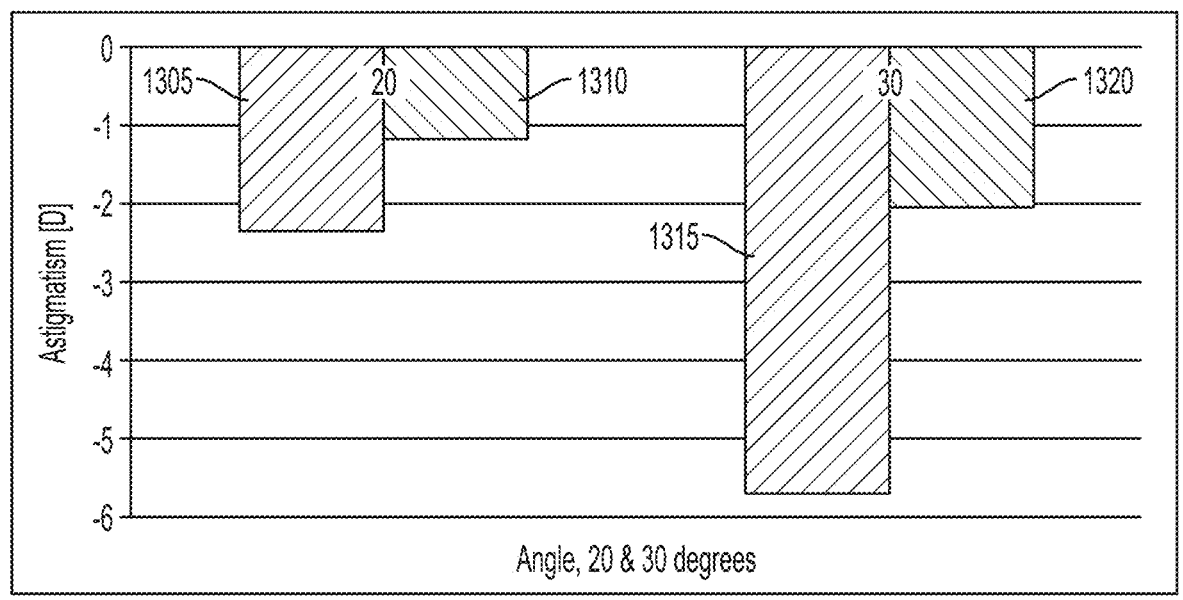
FIG. 11A is a graph depicting the simulated off-axis astigmatism for two different embodiments of an IOL at visual field angles of 20 degrees and 30 degrees.
Figure 11B:
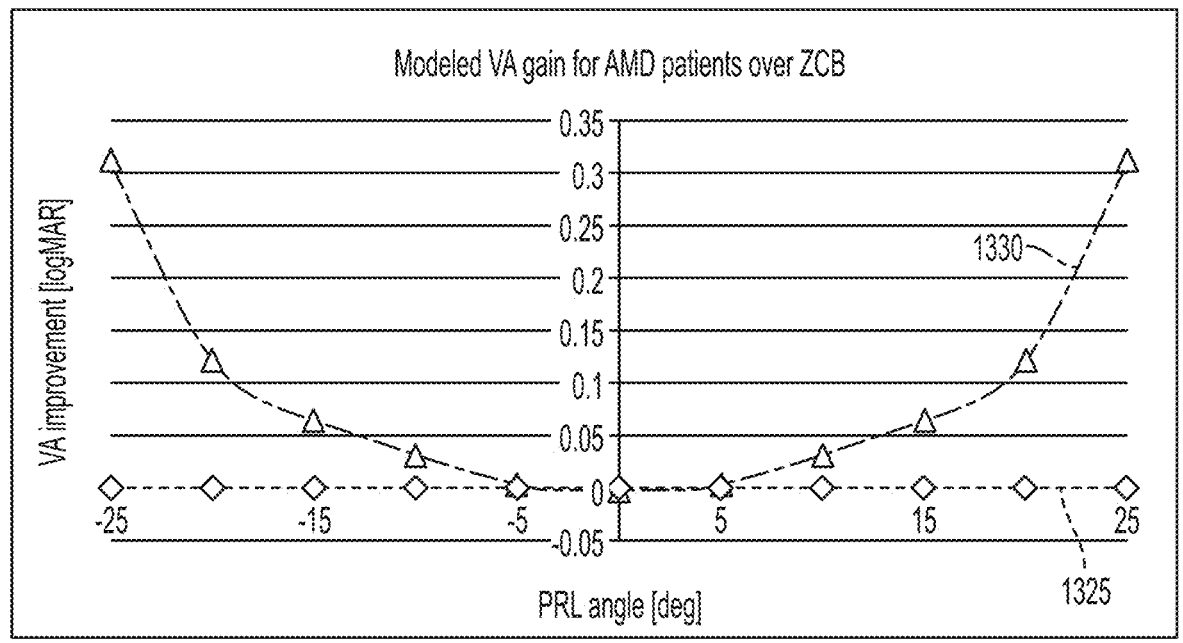
FIG. 11B is a graph depicting the simulated visual acuity gain for two different embodiments of an IOL for different visual field angles.
Figure 12A:
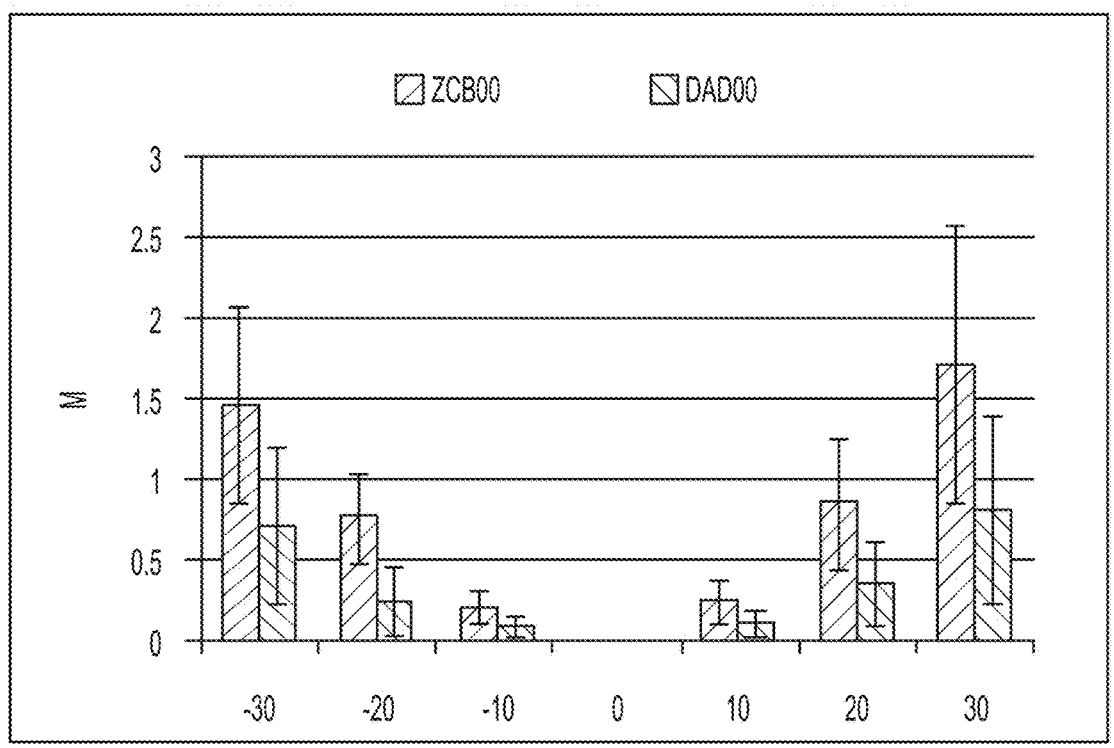
FIGS. 12A and 12B depict the simulated mean sphere and cylinder for different visual field angles for different embodiments of an IOL.
Figure 12B:
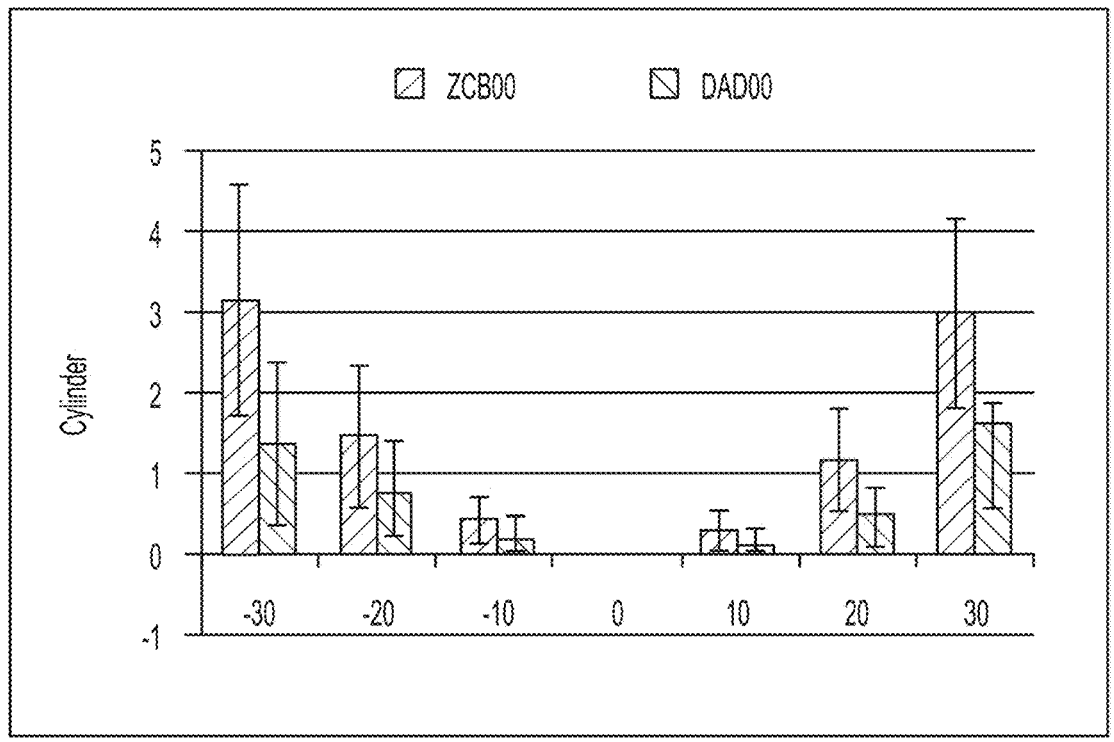
Figure 12C:
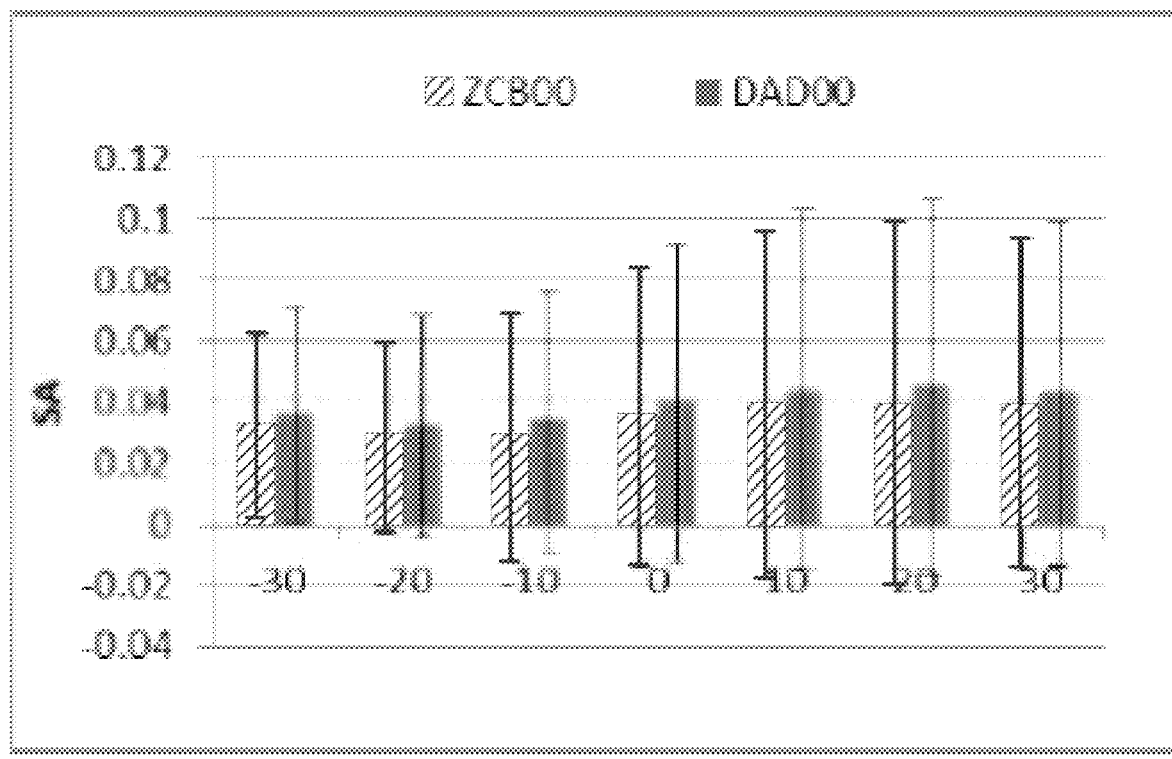
FIGS. 12C and 12D depict the simulated spherical aberration and total RMS for different visual field angles for different embodiments of an IOL.
Figure 12D:
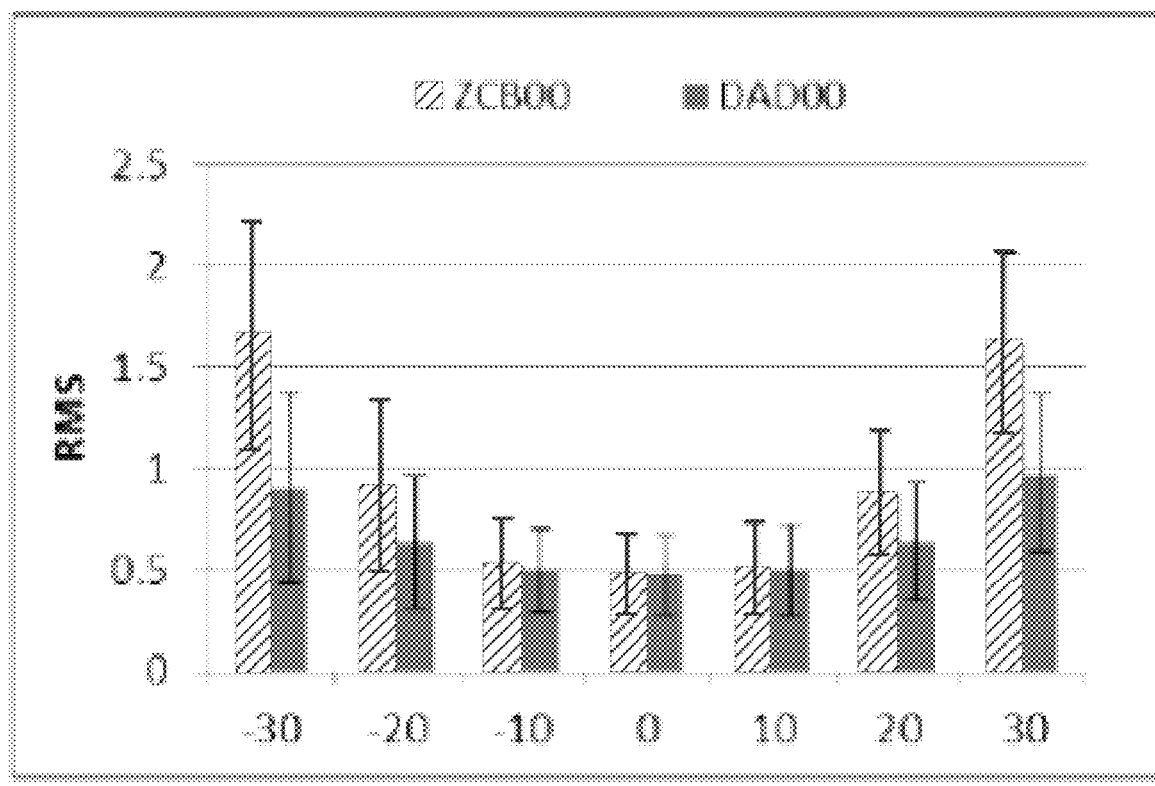

Simulated off-axis astigmatism is depicted in FIGS. 11A and 11B. FIG. 11A is a graph depicting the simulated off-axis astigmatism for two different embodiments of an IOL at visual field angles of 20 degrees and 30 degrees. In FIG. 11A, bar 1305 is the off-axis astigmatic power of the ZCB lens at a visual field angle of about 20 degrees, bar 1310 is the off-axis astigmatic power of the DAD IOL at a visual field angle of about 20 degrees, bar 1315 is the off-axis astigmatic power of the ZCB lens at a visual field angle of about 30 degrees, and bar 1320 is the off-axis astigmatic power of the DAD IOL at a visual field angle of about 30 degrees. It is noted from FIG. 11A, that the embodiment of the DAD IOL in conjunction with the human visual system (including the optics of the cornea of an average eye) provides a residual peripheral astigmatism less than about 2.0 Diopter at visual field angles of 20 degrees and 30 degrees. It is further noted is that the residual peripheral astigmatism provided by the combination of the embodiment of the DAD IOL along with the human visual system (including the optics of the cornea of an average eye) is about half the residual peripheral astigmatism provided by the combination of the ZCB lens along with the human visual system (including the optics of the cornea of an average eye). Without subscribing to any particular theory, the residual peripheral astigmatism is a difference in diopters between tangential and sagittal peaks which is referred to optometrists as 'C'.

Although the peripheral astigmatism is one of the sources of off-axis aberration, it does not fully describe peripheral off-axis image quality. Other peripheral aberrations such as peripheral defocus, coma, and other higher order aberrations can also degrade image quality. Therefore, a metric that relies on the area under the MTF for spatial frequencies up to the neurally relevant cutoff is used to characterize peripheral visual quality. The area under the MTF can be correlated with on-axis visual acuity. The area is then converted to an equivalent diopter value, which is converted to a VA loss score in log MAR with a factor of 0.15. FIG. 11B is a graph depicting the visual acuity gain for the ZCB IOL (represented by curve 1325) and an embodiment of the DAD IOL (represented by curve 1330) for different visual field angles. It is observed that the embodiment of the DAD IOL (represented by curve 1330) has a visual acuity gain of about 0.3 over the ZCB IOL at a visual field angle of about 25 degrees and a visual acuity gain of about 0.1 over the ZCB IOL at a visual field angle of about 20 degrees. Accordingly, an AMD patient can have considerable improvement in visual image quality at a peripheral retinal location when implanted with the embodiment of the DAD IOL as compared to when implanted with the ZCB lens. Additionally, the embodiment of the DAD IOL can have reduced anterior surface reflectivity.

As discussed herein, correction of peripheral refractive errors and/or aberrations can improve peripheral vision. For example, patients with AMD can benefit by correction of peripheral refractive errors and/or aberrations. FIGS. 12A-12D show a comparison of the mean sphere, cylinder, spherical aberration and total higher order root mean square errors for the ZCB lens (represented by solid blocks) and an embodiment of the DAD IOL (represented by hatched blocks) as a function of visual angle. It is noted from FIGS. 12A and 12B that the DAD IOL (represented by hatched blocks) has reduced values of mean sphere and the cylinder at visual angles corresponding to 10, 20 and 30 degrees as compared to the ZCBIOL (represented by solid blocks). From FIG. 12C it is observed that the central as well as peripheral spherical aberration (at visual angles corresponding to 10, 20 and 30 degrees) for the DAD IOL (represented by hatched blocks) is substantially similar to the central as well as peripheral spherical aberration (at visual angles corresponding to 10, 20 and 30 degrees) for the ZCB IOL. It is noted from FIG. 12D that the total higher order root mean square errors for the ZCB IOL at visual angles corresponding to 10, 20 and 30 degrees is higher than the total higher order root mean square errors for the DAD IOL at visual angles corresponding to 10, 20 and 30 degrees. The total higher order root mean square errors for the ZCB IOL for central vision is comparable to the total higher order root mean square errors for the DAD IOL.

Thus, compared to an existing monofocal IOL that is configured to provide good on-axis image quality (referred to herein as a ZCB IOL), the DAD IOL can give superior off-axis performance, while maintaining equal on-axis performance. The embodiments of the DAD IOL discussed herein can be configured to have increased tolerance to a large number surgery dependent variables as well as population variables. The design principles discussed herein can also be used to design and manufacture an intraocular lens that provides visual acuity for foveal vision (or central vision) as well as peripheral vision (e.g., for visual field angles up to 30 degrees) similar to the IOLs described in U.S. Provisional Application No. 62/385,702 filed on Sep. 9, 2016 titled "Intraocular Lenses with Improved Central and Peripheral Vision" which is incorporated herein by reference in its entirety is described below.

Figure 13:
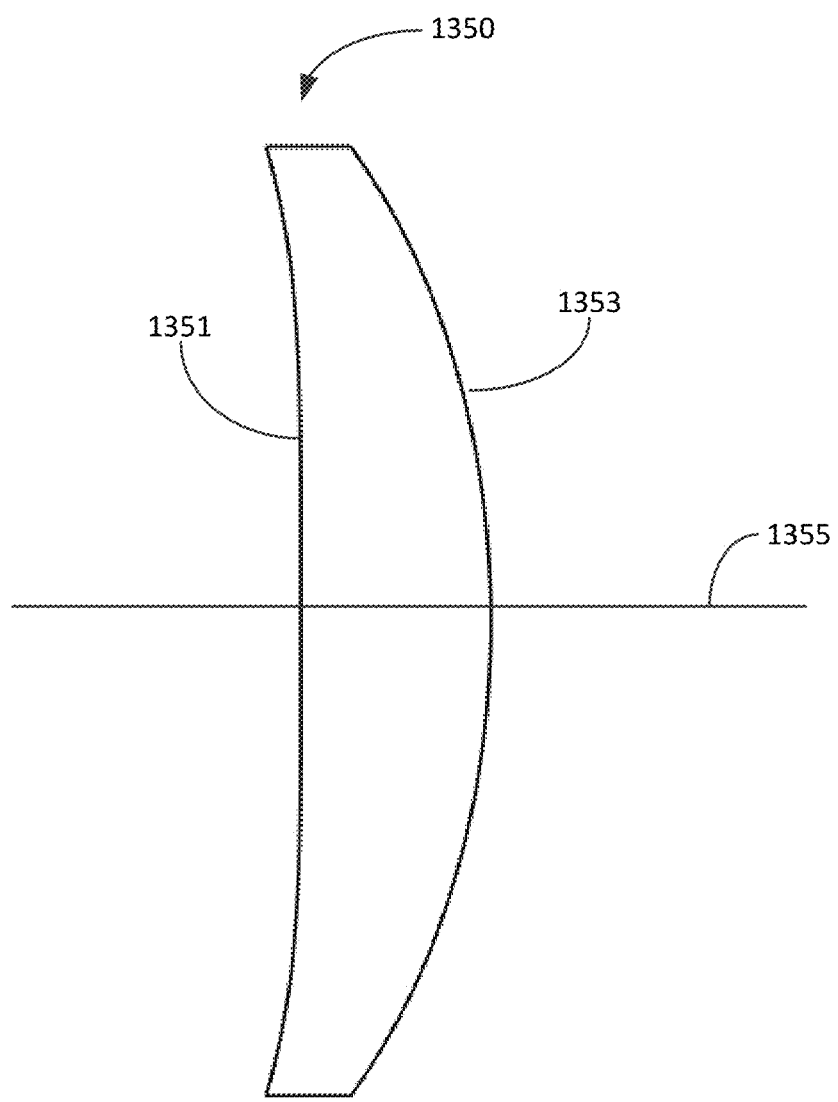
FIG. 13 illustrates an embodiment of an IOL configured to provide improved peripheral vision as well as improved foveal vision.

FIG. 13 illustrates an embodiment of an IOL 1350 that is configured to provide good foveal vision as well as good peripheral vision. Such IOLs can be used for patients suffering from Glaucoma and/or AMD. The IOL 1350 has an anterior surface 1351 and a posterior surface 1353. The anterior and posterior surfaces 1351 and 1353 are intersected by an optical axis 1355. In various embodiments, the IOL 1350 has a meniscus-biconvex design. The IOL 1350 can be configured to have a double aspheric design (DAD). Accordingly, various characteristics/parameters of the IOL 1350 can be similar to the DAD IOLs discussed above. Additionally, various embodiments of the DAD IOLs discussed above can have characteristics/parameters similar to the IOL 1350 discussed below.

Various embodiments of the IOL 1350 can be configured such that the posterior surface 1353 is configured to provide most of the refractive power and the anterior surface 1351 is configured to correct for the spherical aberration introduced by the posterior surface 1353. In various embodiments of the IOL 1350 the anterior surface 1351 and/or the posterior surface 1353 can be aspheric. In such embodiments, the asphericity of the posterior surface 1353 can be configured to introduce a significant amount of spherical aberration in the posterior surface. For example, the posterior surface 1353 can be configured to have spherical aberration in the range between about 0.5 μm and 1.3 μm (e.g., 1.11 μm). Accordingly, the anterior surface 1351 can be configured to have a negative spherical aberration in the range between about −0.5 μm and −1.3 μm to correct for the spherical aberration introduced by the posterior surface 1353 such that the total residual spherical aberration introduced by the IOL 1350 for a normal population of eyes is in the range between 0.1 μm and −0.05 μm for a 5 mm pupil. The apshericity of the anterior surface 1351 that corrects the spherical aberration introduced by the posterior surface 1353 can have a great impact on peripheral image quality. For example, the asphericity of the positive surface 1353 and the anterior surface 1351 can be adjusted such that the average value for the total residual spherical aberration introduced by the IOL 1350 for a normal population of eyes can be less than about 0.05 µm for a 5 mm pupil.

The IOL 1350 can be configured to have a shape factor between −2 and −0.9. For example, the shape factor of the IOL 1350 can be less than or equal to −0.9 and greater than −1.0; less than or equal to −1.0 and greater than −1.1; less than or equal to −1.1 and greater than −1.2; less than or equal to −1.3 and greater than −1.4; less than or equal to −1.5 and greater than −1.6; less than or equal to −1.7 and greater than −1.8; less than or equal to −1.8 and greater than −1.9; less than or equal to −1.9 and greater than −2.0. The shape factor of the IOL 100 can be adjusted by adjusting a variety of parameters including but not limited to vault height of the IOL 1350, placement of the IOL 1350 in the eye, thickness of the IOL 1350 along the optical axis 1355, curvature of the posterior and anterior surfaces of the IOL 1350 and/or asphericity of the posterior and anterior surfaces of the IOL 1350. In various embodiments, the vault height of the IOL 1350 can be increased by an amount between 0 and about 1.5 mm as compared to standard IOLs. As discussed above, the IOL 1350 can be vaulted posteriorly towards the retina by a distance between about 0 mm and about 1.5 mm as compared to standard IOLs. For example, in various embodiments the IOL 1350 can be implanted such that the principal plane of the IOL 1350 is displaced by an amount such as, for example about 0.01 mm and about 0.6 mm posteriorly from the iris as compared to the position where a standard intraocular lens (e.g., a meniscus IOL) is implanted. As another example, the IOL 1350 can be implanted such that the principal plane of the IOL 1350 is displaced by a distance of about 0.2 mm posteriorly from the iris as compared to the position where a standard intraocular lens is implanted. Vaulting the IOL 1350 posteriorly towards the retina can result in a shift of the principal plane of the IOL 1350 posteriorly.

It is noted that the shift of the principal plane for the IOL 1350 can be achieved by a variety of methods including but not limited to distributing the refractive power such that a majority of the refractive power is provided by the posterior surface, physically shifting the position of the IOL 1350 and/or increase in thickness of the IOL 1350. In various embodiments, the IOL 1350 can have a thickness that is about 0.1 mm to about 0.5 mm thicker than thickness of standard IOLs. For example, as discussed above, the central thickness of the IOL 1350 can be in the range between about 0.7 mm and about 1.5 mm.

As discussed above, the curvature of the posterior surface 1353 of the IOL 1350 is configured such that the posterior surface 1353 contributes more to the total refractive optical power provided by the IOL 1350 than the anterior surface 1351. For example, the curvature of the posterior surface 1353 can be configured to provide an optical power between about −20 Diopter and +20 Diopter. The curvature of the posterior surface 1353 and the anterior surface 1351 of the IOL 1350 can be configured such that the IOL 1350 has a shape factor between −2 and −0.9. The IOL 1350 when implanted in a normal human eye can provide a residual peripheral astigmatism less than about 1.5 Diopter at a visual field angle of about 30 degrees as compared to a residual peripheral astigmatism of about 3.0 Diopter at a visual field angle of about 30 degrees provided by a standard IOL currently available in the market when implanted in the normal human eye. Without subscribing to any particular theory, the residual peripheral astigmatism is a difference in diopters between tangential and sagittal peaks which is referred to optometrists as 'C'. As another example, the IOL 1350 when implanted in a normal human eye can provide a residual peripheral defocus less than about 1.0 Diopter at a visual field angle of about 30 degrees as compared to a residual peripheral defocus of about 1.5 Diopter at a visual field angle of about 30 degrees provided by a standard IOL currently available in the market when implanted in the normal human eye.

FIGS. 14A-14E illustrate various figures of merit for a standard intraocular lens and an embodiment of an IOL 1350 (such as, for example an IOL having a shape factor between −2 and −0.9) configured to provide improved peripheral vision as well as improved foveal vision. The figures of merit were obtained by performing ray tracing simulations using eye models (e.g., 11 realistic eye models) implanted with either lenses representing a standard IOL (e.g., an aspheric standard IOL having a shape factor of about 1.0 and implanted such that the principal plane is about 1.3 mm behind the iris) and with an embodiment of the IOL 1350 (e.g., a meniscus lens having a shape factor of about −1.2 and implanted such that the principal plane is about 2.4 mm behind the iris).

Figure 14A:
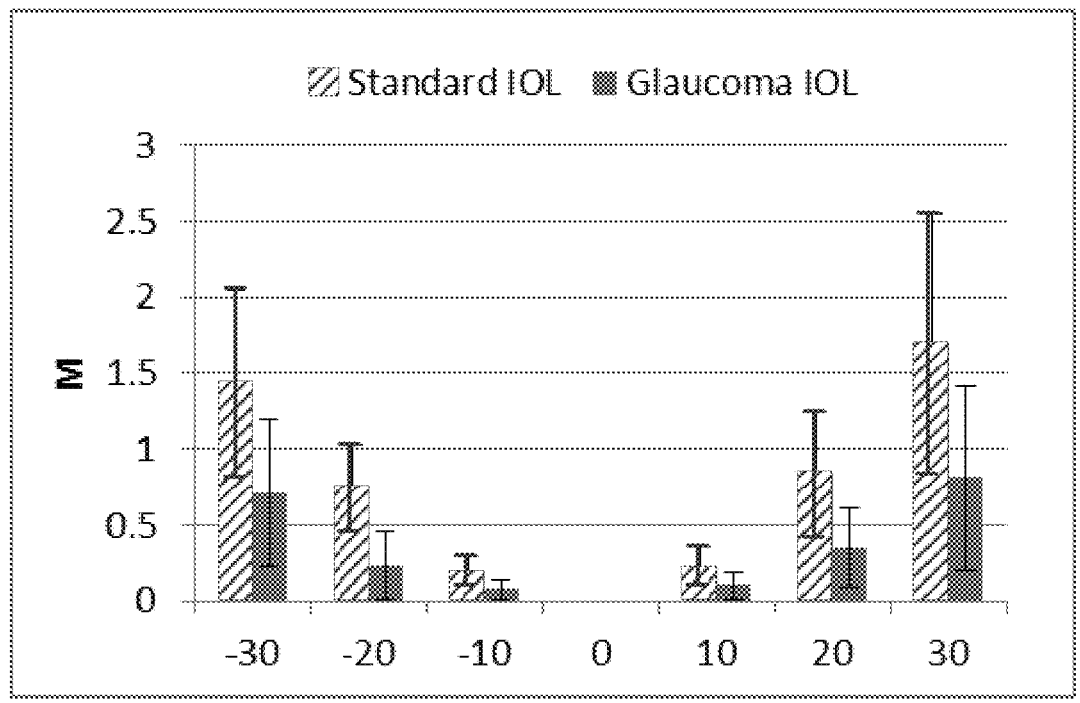
FIGS. 14A-14E illustrate various figures of merit for a standard intraocular lens and an embodiment of an IOL configured to provide improved peripheral vision as well as improved foveal vision.
Figure 14B:
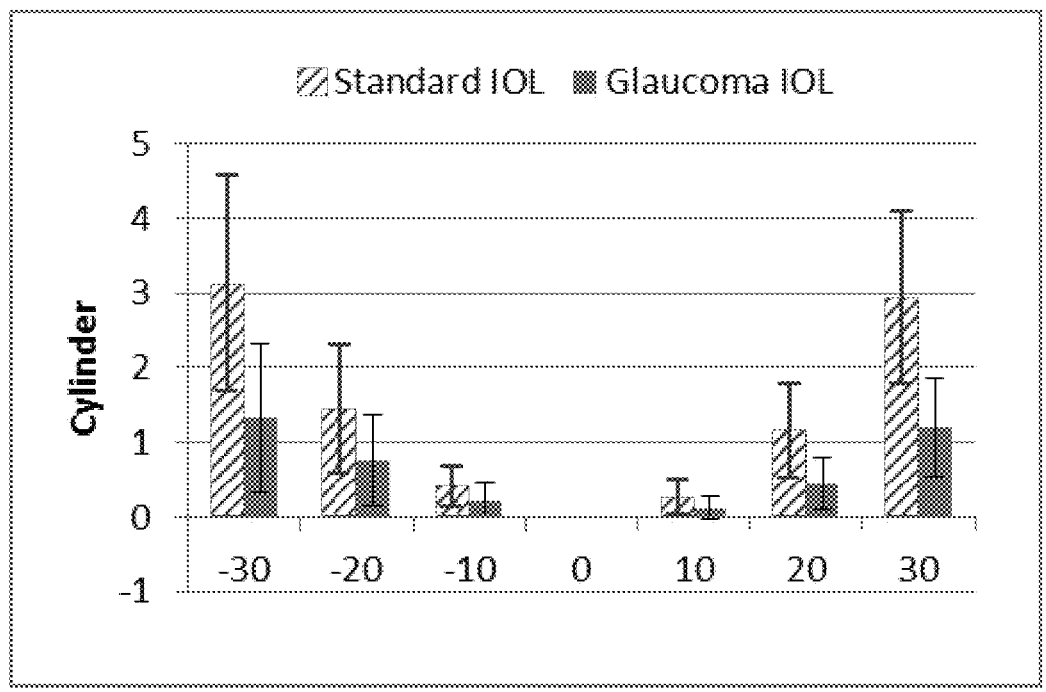
Figure 14C:
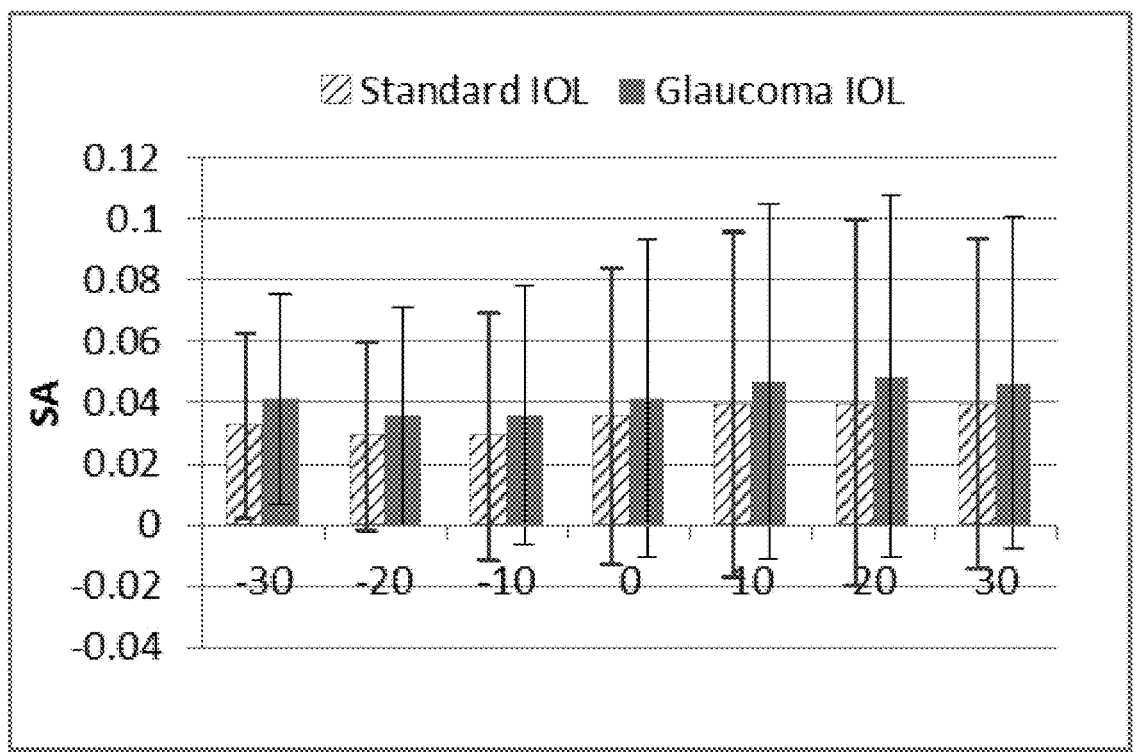
Figure 14D:
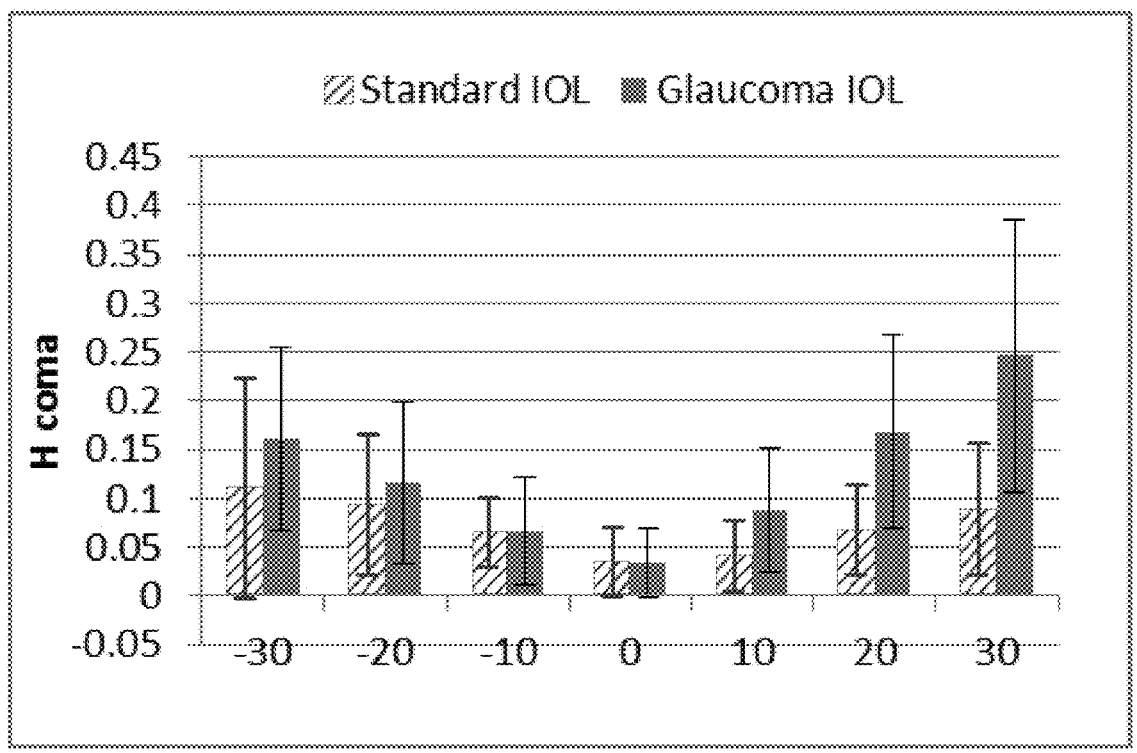
Figure 14E:
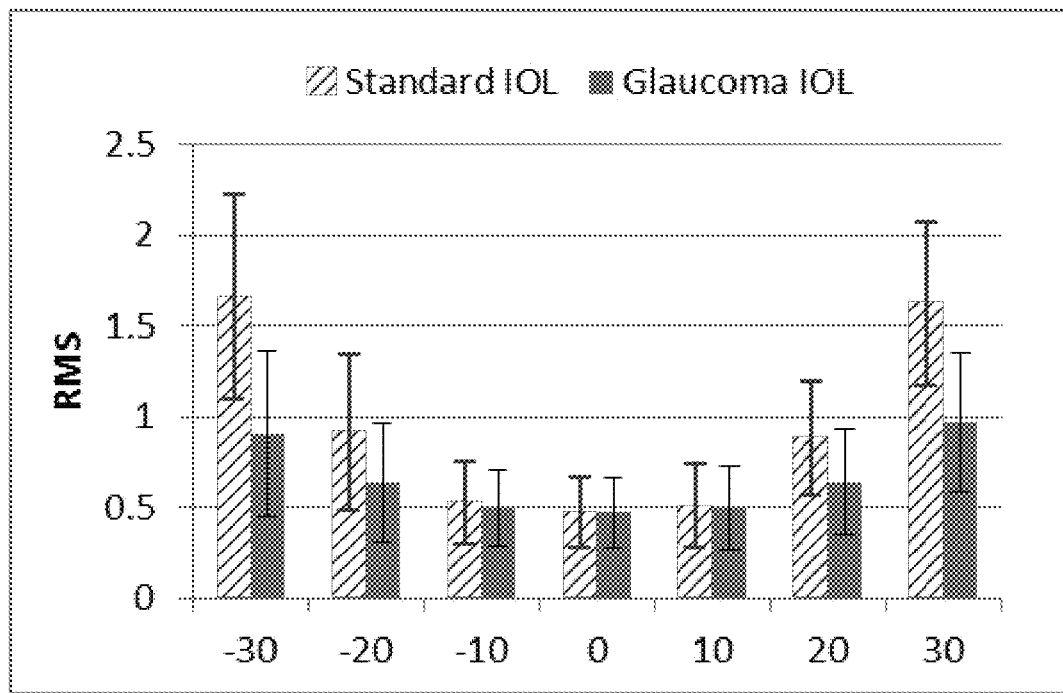

FIG. 14A illustrates the peripheral defocus (M) for an embodiment of the IOL 1350 and an embodiment of a standard IOL as a function of eccentricity. FIG. 14B illustrates the residual peripheral astigmatism provided by an embodiment of the IOL 1350 in combination with a human visual system (including the optics of the cornea of an average eye) and an embodiment of a standard IOL in combination with a human visual system (including the optics of the cornea of an average eye) as a function of eccentricity. FIG. 14C illustrates the spherical aberration (SA) for an embodiment of the IOL 1350 and an embodiment of a standard IOL as a function of eccentricity. FIG. 14D illustrates the horizontal coma for an embodiment of the IOL 1350 and an embodiment of a standard IOL as a function of eccentricity. FIG. 14E illustrates the total root mean square (RMS) for an embodiment of the IOL 1350 and an embodiment of a standard IOL as a function of eccentricity. It is noted that the embodiment of the IOL 1350 has spherical aberration, and overall foveal image quality, similar to the standard IOL. The magnitude of peripheral coma of the embodiment of the IOL 1350 is approximately similar to the standard IOL, but has the opposite sign. However, peripheral defocus and residual peripheral astigmatism for visual field angles up to ±30-degrees is significantly reduced for the embodiment of the IOL 1350 as compared to the standard IOL.

Embodiments of the IOL 1350 can have optical characteristics similar to optical characteristic of other lens designs that are configured to improve peripheral image quality described in U.S. application Ser. No. 14/692,609 filed on Apr. 21, 2015 published as U.S. Publication No. 2015/0320547 which is incorporated by reference here in its entirety. The Glaucoma IOL can be configured as a dual-optic IOL or a piggyback IOL. In various embodiments, embodiments of the IOL 1350 can be configured as a meniscus lens, a biconvex lens, a plano-convex lens or any other possible shape. The embodiments of the IOL 1350 described herein can be combined with or replace one or more IOL designs configured to improve peripheral image quality for patients with AMD that are described in U.S. application Ser. No. 14/644,101 (filed on Mar. 10, 2015, Published as U.S. Publication No. 2015/0265399); Ser. No. 14/644,110 (filed on Mar. 10, 2015, Published as U.S. Publication No. 2015/0297342); Ser. No. 14/644,107 (filed on Mar. 10, 2015, Published as U.S. Publication No. 2015/0297342); Ser. No. 14/849,369 (filed on Sep. 9, 2015) and Ser. No. 14/644,082 (filed on Mar. 10, 2015, Published as U.S. Publication No. 2015/0250583) which are incorporated by reference herein for all that they describe.

Example Method of Designing an IOL

Figure 15:
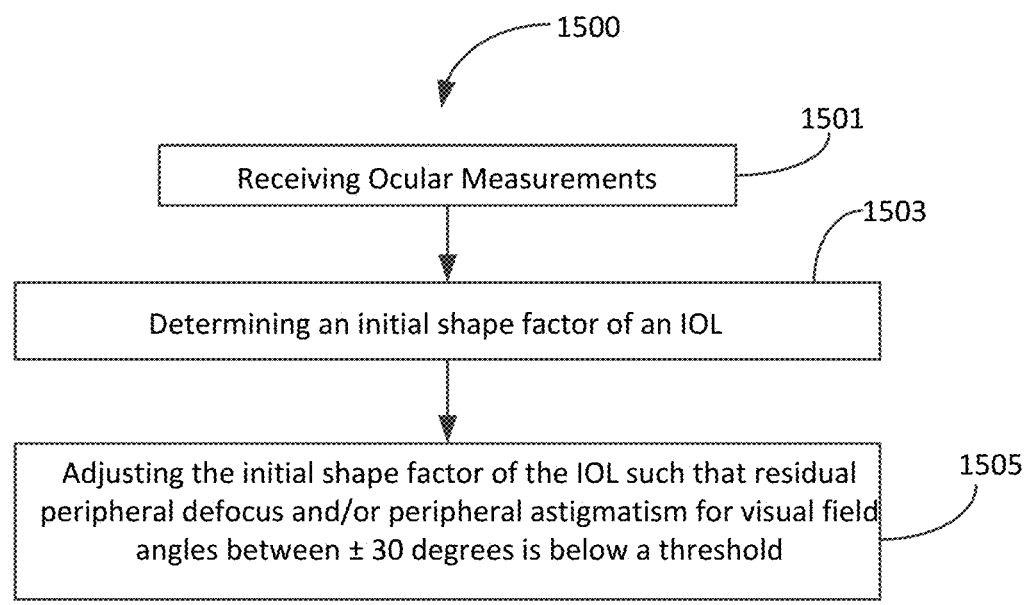
FIG. 15 is a flow chart of a method of designing an IOL to correct peripheral refractive errors.

An example method of designing an IOL to correct for peripheral refractive errors is illustrated in FIG. 15. The method 1500 includes receiving ocular measurements for a patient as shown in block 1501. The ocular measurements can be obtained by an ophthalmologist using instruments such as a COAS or a biometer which are currently available in ophthalmology practice. The ocular measurements can include axial length of the eye, corneal power, refractive power that provides visual acuity for central vision, intraocular pressure, peripheral refractive errors measured by a visual fields test and any other measurements that can be used to characterize a patient's visual acuity for field angles upto ±30-degrees. The ocular measurements can include obtaining the variation of the peripheral astigmatism, horizontal coma and spherical optical power as a function of visual field angle.

An initial shape factor of an IOL that provides good visual acuity for central vision is determined as shown in block 1503. The initial shape factor can b e similar to the shape factor of an appropriate standard IOL currently available that would provide good foveal vision for the patient. The initial shape factor can be iteratively adjusted to optimize peripheral refractive errors for visual field angles upto ±30-degrees without significantly decreasing visual acuity for central vision to determine a final shape factor as shown in block 1505. Adjusting the initial shape factor can include adjusting a curvature of the surfaces of the IOL, adjusting the asphericity of the surfaces of the IOL, adjusting a central thickness of the IOL, adjusting a placement of the IOL in the eye. The final shape factor can be determined by placing a model of the IOL having the initial shape factor in a model eye and adjusting one or more parameters (e.g., thickness, curvature and/or asphericity of the surfaces, shape, etc.) of the model IOL till residual peripheral errors (e.g., defocus and astigmatism) for visual field angles upto ±30-degrees are below a threshold value. For example, the determined final shape factor of the IOL can provide a residual peripheral astigmatism less than 1.5 Diopter at a visual field angle of about 30 degrees as compared to a residual peripheral astigmatism of about 3.0 Diopter at a visual field angle of about 30 degrees provided by a lens having the initial shape factor. As another example, the determined final shape factor of the IOL can provide a residual peripheral defocus less than 1.0 Diopter at a visual field angle of about 30 degrees as compared to a residual peripheral defocus of about 1.5 Diopter at a visual field angle of about 30 degrees provided by a lens having the initial shape factor.

Peripheral astigmatism can be independent of the patient's biometric inputs. Accordingly, the determination of the final shape factor of the IOL that results in an optical power distribution that corrects for peripheral astigmatism can be independent of the patient's biometric inputs. In some embodiments, the final shape factor of the IOL can b e configured to correct peripheral astigmatism by providing additional cylinder power that compensates for peripheral astigmatism only at certain specific visual field angles (e.g., ±15 degrees, ±20 degrees, ±25 degrees, ±30 degrees). In some other embodiments, the final shape factor of the IOL can be configured to correct peripheral astigmatism by providing additional cylinder power that compensates for peripheral astigmatism at all visual field angles in an angular range (e.g., between ±15 degrees, between ±20 degrees, between ±25 degrees, between ±30 degrees). In some embodiments, the final shape factor of the IOL can be configured to correct defocus only at certain specific visual field angles (e.g., ±15 degrees, ±20 degrees, ±25 degrees, ±30 degrees). In some other embodiments, the final shape factor of the IOL can be configured to correct defocus at all visual field angles in an angular range (e.g., between ±15 degrees, between ±20 degrees, between ±25 degrees, between ±30 degrees).

Figure 16:
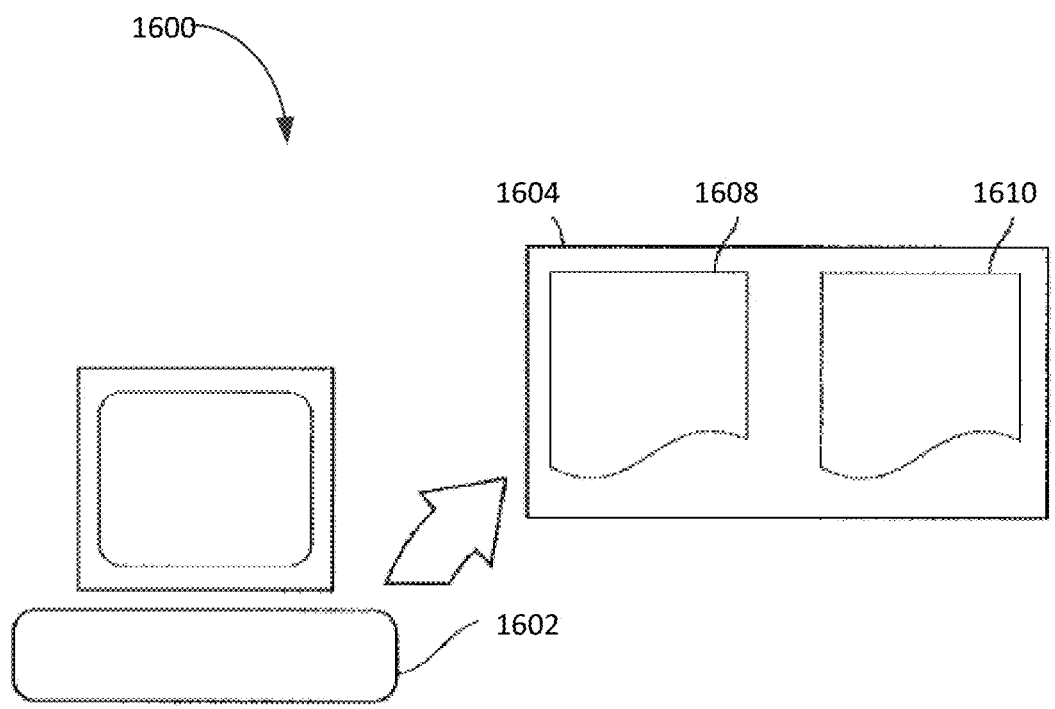
FIG. 16 is a graphical representation of the elements of computing system for selecting an ophthalmic lens.

The method of designing an IOL to correct for peripheral refractive errors can be implemented by a computer system 1600 illustrated in FIG. 16. The system includes a processor 1602 and a computer readable memory 1604 coupled to the processor 1602. The computer readable memory 1604 has stored therein an array of ordered values 1608 and sequences of instructions 1610 which, when executed by the processor 1602, cause the processor 1602 to perform certain functions or execute certain modules. For example, a module can be executed that is configured to selecting an ophthalmic lens or an optical power thereof that would provide visual acuity for central vision and iteratively adjust various parameters of the lens that would reduce peripheral refractive errors including but not limited to defocus and astigmatism.

The array of ordered values 1608 may comprise, for example, one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. In some embodiments, the sequence of instructions 1610 includes determining a position of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power, different design, and/or a different IOL location.

The computer system 1600 may be a general purpose desktop or laptop computer or may comprise hardware specifically configured performing the desired calculations. In some embodiments, the computer system 1600 is configured to be electronically coupled to another device such as a phacoemulsification console or one or more instruments for obtaining measurements of an eye or a plurality of eyes. In other embodiments, the computer system 1600 is a handheld device that may be adapted to be electronically coupled to one of the devices just listed. In yet other embodiments, the computer system 1600 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

In certain embodiments, the system 1600 includes or is part a phacoemulsification system, laser treatment system, optical diagnostic instrument (e.g, autorefractor, aberrometer, and/or corneal topographer, or the like). For example, the computer readable memory 1604 may additionally contain instructions for controlling the handpiece of a phacoemulsification system or similar surgical system. Additionally or alternatively, the computer readable memory 1604 may additionally contain instructions for controlling or exchanging data with an autorefractor, aberrometer, tomographer, and/or topographer, or the like.

In some embodiments, the system 1600 includes or is part of a refractive planner. The refractive planner may be a system for determining one or more treatment options for a subject based on such parameters as patient age, family history, vision preferences (e.g., near, intermediate, distant vision), activity type/level, past surgical procedures.

An achromatic optical element or an achromatic surface as described herein can be integrated with other embodiments of IOLs that improve peripheral vision that are described in U.S. application Ser. No. 14/692,609 filed on Apr. 21, 2015 published as U.S. Publication No. 2015/0320547 which is incorporated by reference here in its entirety. An achromatic optical element or an achromatic surface as described herein can be integrated with the various IOL designs configured to that improve peripheral image quality for patients with AMD that are described in U.S. application Ser. No. 14/644,101 (filed on Mar. 10, 2015, Published as U.S. Publication No. 2015/0265399); Ser. No. 14/644,110 (filed on Mar. 10, 2015, Published as U.S. Publication No. 2015/0297342); Ser. No. 14/644,107 (filed on Mar. 10, 2015, Published as U.S. Publication No. 2015/0297342); Ser. No. 14/849,369 (filed on Sep. 9, 2015) and Ser. No. 14/644,082 (filed on Mar. 10, 2015, Published as U.S. Publication No. 2015/0250583) which are incorporated by reference herein for all that they describe.

The achromatic profile step height can be adjusted to optimize performance for the peripheral region of interest to aid patients with AMD. In some embodiments, the step height can be reduced by a factor of cosine of the angle of the preferred retinal locus, to account for the oblique incidence.

In some embodiments, the achromatic zone size can be limited to portions of the pupil while leaving some portions of the pupil free of the achromatic optical element to provide clear region to view or inspect the retina. In some embodiments, the achromatic optical element can be configured such that the central parts of the achromat contribute to on-axis performance and peripheral parts of the achromat contribute to off-axis performance.

Various embodiments of the lenses and the achromats can comprise a material that can block specific parts of the spectrum. For example, the lenses and achromats can comprise a material that can block potentially AMD-inducing blue light. The peak wavelength selected to design various embodiments of the lenses and achromats can be based on the material used to manufacture the lenses and achromats. For example, if the lenses and achromats comprise a material that can block potentially AMD-inducing blue light, the design wavelength can be selected to be greater than 550 nm, in order to optimize the amount of light in the first order focus.

Various concepts, systems and methods described herein can also be used for patients without AMD who wish to improve peripheral vision while gaining superior on-axis vision.

The above presents a description of the best mode contemplated of carrying out the concepts disclosed herein, and of the manner and process of making and using it, in such full, clear, concise, and exact terms as to enable any person skilled in the art to which it pertains to make and use the concepts described herein. The systems, methods and devices disclosed herein are, however, susceptible to modifications and alternate constructions from that discussed above which are fully equivalent. Consequently, it is not the intention to limit the scope of this disclosure to the particular embodiments disclosed. On the contrary, the intention is to cover modifications and alternate constructions coming within the spirit and scope of the present disclosure as generally expressed by the following claims, which particularly point out and distinctly claim the subject matter of the implementations described herein.

Although embodiments have been described and pictured in an example form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "processor" refers broadly to any suitable device, logical block, module, circuit, or combination of elements for executing instructions. For example, the processor 1602 can include any conventional general purpose single- or multi-chip microprocessor such as a Pentium® processor, a MIPS® processor, a Power PC® processor, AMD® processor, ARM processor, or an ALPHA® processor. In addition, the processor 302 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 1602 can be implemented as a combination of computing devices, e.g., a combination of a DSP and a microprocessor, a plurality of microprocessors, one or more microprocessors in conjunction with a DSP core, or any other such configuration.

Computer readable memory 1604 can refer to electronic circuitry that allows information, typically computer or digital data, to be stored and retrieved. Computer readable memory 1604 can refer to external devices or systems, for example, disk drives or solid state drives. Computer readable memory 1604 can also refer to fast semiconductor storage (chips), for example, Random Access Memory (RAM) or various forms of Read Only Memory (ROM), which are directly connected to the communication bus or the processor 1602. Other types of memory include bubble memory and core memory. Computer readable memory 1604 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

What is claimed is:

1. A method of designing an intraocular lens, the method comprising:
   receiving ocular measurements for a patient;
   selecting an intraocular lens having an initial shape factor;
   determining a final shape factor of the intraocular lens by iteratively adjusting the initial shape factor to reduce peripheral refractive errors at one or more visual field angles between −30 degrees and 30 degrees, with respect to an optical axis at the fovea, below a threshold value,
   wherein the intraocular lens comprises an optic comprising:
      a first aspheric surface; and
      a second aspheric surface opposite the first aspheric surface,
   wherein the first aspheric surface is concave, and the second aspheric surface is convex,
   wherein one of the first and second aspheric surfaces comprises an achromatic optical element,
   wherein the optic comprises a meniscus lens having the first aspheric surface and the second aspheric surface,
   wherein the optic is configured to focus light incident along a direction parallel to the optical axis at the fovea to produce a functional foveal image,
   wherein the optic is configured to focus light incident on a patient's eye at an oblique angle with respect to the optical axis at a peripheral retinal location disposed at a distance from the fovea, the peripheral retinal location having an eccentricity between −30 degrees and 30 degrees with respect to the optical axis,
   wherein iteratively adjusting the initial shape factor includes adjusting at least one of (i) a curvature of the surfaces of the optic, (ii) a central thickness of the optic, (iii) an axial position of the optic from the iris of the patient's eye, and (iv) the asphericity of the surfaces of the optic, until said peripheral refractive errors at said one or more visual field angles between −30 degrees and 30 degrees are below said threshold value.

2. The method of claim 1, wherein the final shape factor of the intraocular lens is between −3 and −0.5.

3. The method of claim 1, wherein a peripheral defocus for visual field angles between −30 degrees and 30 degrees with respect to the optical axis is less than about 1.0 Diopter when the intraocular lens having the final shape factor is implanted in the patient's eye.

4. The method of claim 1, wherein a peripheral astigmatism for visual field angles between −30 degrees and 30 degrees with respect to the optical axis is less than about 1.5 Diopter when the intraocular lens having the final shape factor is implanted in the patient's eye.

* * * * *